United States Patent [19]
Corner et al.

[11] Patent Number: 5,980,911
[45] Date of Patent: Nov. 9, 1999

[54] ADJUVANT

[75] Inventors: Leigh Austin Corner, Romsey; James Stuart Rothel, Glenhuntly; Heng Fong Seow, Footscray; Paul Richard Wood, Lower Templestowe; Peter McWaters, Ivanhoe, all of Australia

[73] Assignee: Commonwealth Scientific and Industrial Research Organisation, Campbell, Australia

[21] Appl. No.: 08/732,398

[22] PCT Filed: May 4, 1995

[86] PCT No.: PCT/AU95/00261

§ 371 Date: Feb. 11, 1997

§ 102(e) Date: Feb. 11, 1997

[87] PCT Pub. No.: WO95/30436

PCT Pub. Date: Nov. 16, 1995

[30]   Foreign Application Priority Data

May 4, 1994  [AU]  Australia .......................... PM 5438/94

[51] Int. Cl.[6] .......................... A61K 38/19; A61K 38/20; A61K 39/00; C07K 14/52
[52] U.S. Cl. .................................... 424/265.1; 424/278.1; 530/351
[58] Field of Search .............................. 424/278.1, 265.1; 514/44; 530/351; 435/320.1; 536/23.5

[56]   References Cited

FOREIGN PATENT DOCUMENTS

| 91/00358 | 3/1992 | Australia . |
| 91/00419 | 4/1992 | Australia . |
| 92/01061 | 11/1992 | France . |
| 6-247873 | 9/1994 | Japan . |
| 2232675 | 12/1990 | United Kingdom . |
| WO 92/03574 | 3/1992 | WIPO . |
| WO 92/05255 | 4/1992 | WIPO . |

OTHER PUBLICATIONS

Arroyo et al. (1990) Active specific immunotherapy with vaccinia colon oncolysate enhances the immunomodulatory and antitumor effects of interleukin–2 and interferon alpha in a murine hepatic metastases model. Cancer Immunol. Immunother. 31:305–311, Aug. 1990.

Schijns et al. (1994) Modulation of antiviral immune responses by exogenous cytokines: effects of tumour necrosis factor–alpha, interleukin–1 alpha, interleukin–2 and interferon–gamma on the immunogenicity of an inactivated rabies vaccine. J. Gen. Virol. 7, Jan. 1994.

Heath, et al. (1992) "Cytokines as Immunological Adjuvants", *Vaccine* 10:427–434.

McCullough et al. (1991) "The Immune Response Against Foot–and–Mouth Disease Virus: Influence of the T Lymphocyte Growth Factors IL–1 and IL–2 on the Murine Humoral Repsonse in vivo", *Immunol. Lett.* 31:41–46.

Reddy et al. (1993) "Immunopotentiation of Bovine Respiratory Disease Virus Vaccines by Interleukin–1B and Interleukin–2*", *Veterinary Immunology and Immunopathology* 37:25–38.

*Primary Examiner*—George C. Elliott
*Assistant Examiner*—Robert Schwartzman
*Attorney, Agent, or Firm*—Scully, Scott, Murphy & Presser

[57]   ABSTRACT

The present invention relates generally to adjuvants which comprise a combination of at least two cytokines or functional derivatives thereof. More particularly, the present invention is directed to an adjuvant such as a vaccine adjuvant comprising at least two cytokines or functional derivatives thereof wherein the cytokines are selected from IL-1β and TNFα or IL-1β and GM-CSF. The present invention is farther directed to genetic adjuvants encoding at least two cytokines or derivatives thereof either separately or fused together. The present invention also contemplates a method for enhancing an immune response to an antigen comprising the administration of at least two cytokines which act in synergy to enhance an immune response to said antigen. The present invention is particularly useful in pharmaceutical vaccines and genetic vaccines in humans and livestock animals.

14 Claims, 15 Drawing Sheets

ADJUVANT

This application is a 371 of PCT/AU95/00261 filed May 4, 1995.

The present invention relates generally to adjuvants which comprise a combination of at least two cytokines or functional derivatives thereof. More particularly, the present invention is directed to an adjuvant such as a vaccine adjuvant comprising at least two cytokines or functional derivatives thereof wherein the cytokines are selected from IL-1β and TNFα or IL-1β and GM-CSF. The present invention is further directed to genetic adjuvants encoding at least two cytokines or derivatives thereof either separately or fused together. The present invention also contemplates a method for enhancing an immune response to an antigen comprising the administration of at least two cytokines which act in synergy to enhance an immune response to said antigen. The present invention is particularly useful in pharmaceutical vaccines and genetic vaccines in humans and livestock animals.

Bibliographic details of the publications referred to in this specification are collected at the end of the description. Sequence Identity Numbers (SEQ ID NOs.) for the nucleotide sequences referred to in the specification are defined following the bibliography.

Throughout this specification, unless the context requires otherwise, the word "comprise" or variations such as "comprises" or "comprising", will be understood to imply the inclusion of a stated element or integer or group of elements of integers but not the exclusion of any other element or integer or group of elements or integers.

The increasing sophistication of molecular biological and protein chemical techniques has, and continues to, revolutionise vaccine development. Frequently, however, recombinant and synthetic molecules exhibit less immunogenicity relative to the whole organism or cell from which they are derived. In order to increase the efficiency of such vaccines, considerable research has been directed to the development of immunological adjuvants.

Adjuvants promote the immune response in a number of ways (East et al, 1993). First, some adjuvants maintain a depot of antigen at the site of injection, as demonstrated by the correlation between persistence of antigen at the site of injection and maintenance of serum antibody levels. Second, adjuvants are capable of promoting accumulation of immunoreactive cells at the site of injection and in the draining lymph nodes, which ensures optimal exposure of specific immunoresponsive cells to the antigen. Adjuvants also modify the activities of cells that are concerned with generating and maintaining the immune response. Additionally, adjuvants modify the presentation of antigen to the immune system.

Cytokines such as interleukins (IL-1 to 13), colony stimulating factors (CSFs), tumour necrosis factors (TNF-α and β) and interferons (IFN-α, β and γ) are the hormones of the immune system which control and determine the nature of the immune response (Balkwill and Burke, 1989). Adjuvants with the capacity for immune modulation achieve their activity primarily by modification of cytokine production, probably by direct action upon T cells or macrophages (Cox and Coulter, 1992). Cytokines regulate various aspects of the immune response to vaccination including cellular traffic at the site of vaccination (Zimmerman et al., 1992), antigen presentation (Valle et al., 1991), the phenotype of the T helper cell response (Romagnani, 1992), maturation and differentiation of the B cell response (Snapper and Mond, 1993) and differentiation of non-specific killer cells such as eosinophils and mast cells (Clutterbuck et al., 1989). Recombinant cytokines not only have the potential to enhance the immune response to a vaccine antigen but also alter the immune response leading to different effector mechanisms.

As an alternative to chemical adjuvants, the use of cytokines as natural adjuvants is attracting considerable interest (reviewed by Heath and Playfair, 1992). Various cytokines have been shown to be effective immunological adjuvants in a variety of model systems, enhancing protection induced by bacterial, viral and parasitic antigens. Some of these molecules have already been shown to enhance the immune response of immunodepressed animals to antigens delivered by viral vectors (Ramshaw et al., 1987), or when incorporated into the emulsion to enhance the antibody response to inactivated vaccines (Good, 1988; Blecha, 1990). Furthermore, in the murine model, cytokines such as IL-1, IL-2 and IFN-γ have been shown to have adjuvant effects for both cellular and humoral response (Staruch and Wood, 1983; Nunberg et al., 1989; Playfair and deSouza, 1987). Limited adjuvanticity of TNF has been reported by Ghiara et al, (1987).

The adjuvant effects of some cytokines have been studied in domestic livestock. Yilma et al., (1985) reported that bovine IFN-γ enhanced the humoral responses of cattle vaccinated with a viral glycoprotein and Reddy et al (1990) demonstrated increased neutralising antibody tires and cytotoxic cell responses to bovine herpes virus-1 when recombinant bovine IL-1β (rBoIL-1β) was included in the vaccine regimen. Recombinant human IL-2 has been administered to pigs vaccinated with *Actinobacillus pleuropneumonia* bactern (Anderson et al., 1987; Nunberg et al., 1988) or a pseudorabies subunit vaccine (Kawahima and Platt, 1989) with increased levels of protection and neutralising antibodies respectively. Recently, Nash et al (1993) reported that the incorporation of recombinant ovine IL-1β (rOvIL-1β) in a alum based vaccine resulted in significantly higher antibody levels to their model antigens ovalbumin.

Despite the potential of using single cytokines as adjuvants in vaccine preparations, little work has been reported on adjuvants consisting of two or more cytokines. This may, in part, have been due to the high cost in preparing recombinant cytokines. Furthermore, cytokines also regulate the activity of other cytokines and, frequently, this involves a down regulation. As a result, it is not readily apparent which combinations of cytokines may work in concert. Heath and Playfair (1992) have suggested the possibility of using combinations of cytokines as adjuvants, however, their proposition contemplates a vast number of combinations and permutations of cytokines with little success in the combinations actually tried.

In the past, substantial technical difficulties have delayed development of vaccines against commercially significant livestock parasites such as gastrointestinal nematodes. In work leading up to the present invention, the inventors sought to improve the immuogenecity of antigens such as nematode antigens by incorporating specific combinations of recombinant cytokines into vaccine formulations. Furthermore, alternative adjuvants are required for human use.

There is a need to identify particular synergistic combinations of cytokines which are capable of acting as adjuvants useful, for example, in the preparation of vaccines.

Accordingly, the present invention provides an adjuvant said adjuvant comprising at least two cytokine activities acting in synergy to enhance an immune response to an antigen. More particularly, the present invention is directed to an adjuvant, said adjuvant comprising a first polypeptide having IL-1β activity and a second polypeptide having TNF-α activity, said first and second polypeptides acting in synergy to enhance an immune response to an antigen.

In a related embodiment, there is provided a first polypeptide having IL-1β activity and a second polypeptide having GM-CSF activity, said first and second polypeptides acing in synergy to enhance an immune response to an antigen.

The adjuvants of the present invention nay also comprise an antigen. Preferred antigens are those from parasites or other pathogenic agents which infect animals or birds and in particular humans or livestock s. Examples of parasites and pathogenic agents include intercellular and extracellular bacterial and other prokaryotic organisms, eukaryotic organisms such as yeast and fungi, protooan organisms, metazoan organisms and ameoba, parasites such as nematodes, for example, species of Haemonchus, Trichostrongylus or Ostertagia or a cestode such as *Taenia ovis*. The present invention extends to any antigen from any pathogen or parasite of animals or birds. The present invention also extends to antigens from non-pathogens such as pollen grain and other irritants for which an immune response is desirable.

The first and second polypeptides may be recombinant molecules or isolated, naturally occurring molecules. The term "polypepide" is used in its broadest sense and includes a protein or a peptide having the desired activity. The first and second polypeptides of the present invention each exhibits one or more of the identifying characteristic of one of IL-1β, TNFα or GM-CSF but each may not necessarily exhibit the full complement of activities exhibited by the corresponding naturally occurring cytokine. The principal requirement is at the first and second polypeptides exhibit sufficient IL-1β, TMFα or GM-CSF activity such that the combined immune enhancing effect of the first and second polypeptides is greater than either the first or second polypeptides alone.

In a most preferred embodiment, the first polypeptide is a recombinant or isolated, naturally occurring IL-1β and the second polypeptide is a recombinant or isolated, naturally occurring TNF-A or GM-CSF or a fictional mutant, derivative, part, fragment, analogue or homologue thereof. The IL-1β TNFα and GM-CSF are generally of animal origin such as from a human, livestock animal (e.g. sheep, cow, pig, horse, goat or donkey), laboratory test animal (e.g. mouse, rat, guinea pig or rabbit), a domestic animal (e.g. dog or cat), avian species (e.g. chicken or other poultry bird) or a captive animal (e.g. kangaroo, deer or wild boar). More preferably, the cytokines are of human or livestock animal origin. Preferred livestock animals include ovine, bovine and porcine species.

As stated above, the first and second polypeptides may be EL-1β and TNFα or EL-1β and GM-CSF proteins, respectively. Reference herein to "IL-1β", "TNFα" and "GM-CSF" includes reference to the naturally occurring molecules or to any amino acid substitutions, deletions and/or additions to either molecule but which retains the synergistic properties when in combination that the other molecule.

Amino acid insertions include amino acid and/or carboxyl terminal fusions as well as intra-sequence insertions of single or multiple amino acids. Generally, insertions within the amino acid sequence will be smaller than amino or carboxyl terminal fusions, of the order of 1 to 4 residues. Insertional amino acid sequence variants are those in which one or more amino acid residues are introduced into a predetermined site in the protein. Deletion variants are characterised by the removal of one or more amino acids from the sequence. Subsitutional variants are those in which at least one residue in the sequence has been removed and a different residue inserted in its place. Such substitutions generally are made in accordance with the following Table 1.

TABLE 1

| Original Residue | Exemplary Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Generally amino acids are replaced by other amino acids having like properties, such as hydrophobicity, hydrophilicity, electronegativity, bukly side chains, etc.

Amino acid substitutions are typically of single residues; insertions usually will be in the order of about 1–10 amino acid residues; and deletions will range from about 1–20 residues. Deletions or insertions preferably are made in adjacent pairs, i.e. a deletion of 2 residues or insertion of 2 residues.

Amino acid variants of IL-1β, TNFα and GM-CSF may also readily be made using peptide synthetic techniques well known in the art, such as solid phase peptide syntheses (Merrifield, 1964) and the like, or by recombinant DNA manipulations. Techniques for making substitution mutations at predetermined sites in DNA having a known sequence are well know for example using M13 mutagenesis. The manipulation of DNA sequences to produce variant proteins which manifest as substitutional, insertional or deletional variants are well known in the art and are described for example in Maniatis et al (1982).

Other examples of recombinant or synthetic mutants and derivatives of the cytokines of the present invention include single or multiple substitutions, deletions and/or additions to any molecule associated with the cytokine such as carbohydrates, lipids and/or proteins or polypeptides.

The terms "analogue" and "derivatives" also extend to any amino acid derivative of IL-1β, TNFα or GM-CSF.

Analogues of the cytokines contemplated herein include, but are not limited to, modifications to side chains, incorporation of unnatural amino acids and/or derivatising the molecule and the use of crosslinkers and other methods which impose conformational constraints on the peptides or their analogues. Examples of side chain modifications contemplated by the present invention include modifications of amino groups such as by reductive alkylation by reaction with an aldehyde followed by reduction with $NaBH_4$; amidation with methylacetimidate; acylation with acetic anhydride carbamoylation of amino groups with cyanate; trinitroenzylation of amino groups with 2, 4, 6 trinitrobenzene sulphonic acid (TNBS); acylaton of amino groups with succinic anhydride and tetrahydrophthalic anhydride and pyridoxylation of lysine with pyridoxal-5'-phosphate followed by reduction with NaBH$_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphononic acid, phenylmercury chloride, 2-chloromercur-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidasole ring of a histidine residue may be accomplished by alkylation with iodoacetic acid derivatives or N-carbethoxylation with diethylpyrocarbonate.

Examples of incorporating unnatural amino acids and derivatives during protein synthesis include, but are not limited to, use of norleucine, 4-aminobutyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (—N=C=N—). In addition, peptides could be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention, therefore, extends to peptides or polypeptides and amino acid hybrid molecules and/or chemical analogues thereof having the identifying characteristics of either IL-1β and/or TNFα and/or GM-CSF as broadly described herein, and/or to regions parts or fragments thereof capable of, or responsible for, the synergistic adjuvant properties when both cytokines are in combination.

Examples of human and animal diseases for which vaccination may be appropriate include but are not limited to Parkinsons, hepatitis, cancer, AIDS or AIDS related conditions, liver cirrhosis, asthma, chicken pox, influenza, diphtheria, common cold, Legionaire's disease, malaria, measles, meningitis, mumps, pneumonia, ring worm, scarlet fever, syphilis, tetanus, tuberculosis, typhoid fever, diarrhea peptic ulcer, schistomaniasis, whooping cough, muscular dystrophy, rheumatoid arthritis, sore throat. The antigens will include gp120 (HIV), urease from *Helicobacter pyloris*. Vaccines may also be applicable for contraceptive use in humans or animals such as livestock animals and companion animals. Examples of specific livestock diseases include, but are not limited to, mastitis, babesiosis, anaplasmosis, pinkeye, Johne's disease, bovine ephemereal fever, cattle tick, ostertagia, disease caused by taenis hydatigena, pastivirus, tuberculosis, thielierosis, foot and mouth disease, blow-fly strike, footrot, ostertagia, haemonchosis, trichostrongylosis, chlamydia, salmonella abortus, caseous lymphadenitis, flecerot, disease caused by rotavirus, *E. coli, Actinobacillus pleuropneumonia*, classical swine fever, African swine virus, Newcastle's disease. Examples of diseases of companion animals include but are not limited to canine distemper, heart worm, rabies, hepatitis, cat flu, triple antigen.

The first and second polypeptides of the present invention may also exist as fusion proteins with other molecules or with each other. Examples of molecules which may be fused to either the first or second polypeptide include immune enhancing molecules, other cytokines or enzymes or components thereof such as glutathione-S-transferase (GST). Where the first and second polypeptides are fused together, there will generally be a spacer peptide between both polypeptides. The fusion must not, however, effect the synergistic adjuvant properties of both polypeptides. The present invention contemplates other forms of fusions in addition to an amide bond between the N-terminus of one polypeptide and the C-terminus of the other polypeptide such as the formation of disulphide bridges between the first and second polypeptides or either polypeptide and a further molecule.

The present invention further contemplates genetic adjuvants comprising one or more nucleic acid molecules encoding separately or as fusion molecules, polypeptides having either IL-1β and TNFα activities or IL-1β and GM-CSF activities. The genetic adjuvants may also comprise a genetic sequence encoding an antigen. In the latter case, the composition is known as a genetic vaccine.

The present invention is predicated in part, on the surprising discovery that the combinations IL-1β and TNFα or IL-1β and GM-CSF exhibit a synergistic co-adjuvant effect. The term "adjuvant" is used in its broadest sense as any substance which enhances, increases, upwardly modulates or otherwise facilitates an immune response to an antigen. The immune response may be measured by any convenient means such as antibody titre or level of cell-mediated response. Although the present invention is particularly exemplified by reference to an immune response to a recombinant fusion protein from *Taenia ovis* or from the *Haemonchus contortus* antigen tropomyosin, it is clear that the subject invention extends to any antigen or group of antigens capable of stimulating a humoral and/or cell mediated immune response in animals or birds and in particular humans or livestock animals.

Particularly preferred antigens are from livestock nematodes such as from Haemonchus, Trichostrongylus or Ostertagia.

Furthermore, the cytokine combinations preferably modulate a T helper (Th) subset response such as a Th1 or Th2 response to induce either a cell-mediated and/or humoral response. The Th1 response is associated with enhanced macrophage activation, increased cytotoxic T cell activity and delayed-type hypersensitivity responses. The Th2 response is associated with increased production of antibodies such as IgG1 or IgE leading to increased mastocytosis and eosinophilia, hallmarks of nematode parasite infection.

The adjuvant composition of the present invention may be packaged for sale with each cytokine contained in a separate compartment with instructions to combine two or more of the cytokines with a desired antigen prior to use. The package may instead contain the adjuvant composition in a single compartment with instructions to combine the adjuvant with a desired antigen prior to use. Alternatively, the adjuvant composition may be administered subsequently or prior administration of the antigen.

Accordingly, another aspect of the present invention contemplates a method of enhancing, increasing, upwardly modulating or otherwise facilitating an immune response in an or a bird to an antigens said method comprising administering to said animal or bird an immune-enhancing effective amount of an adjuvant composition which comprises a first polypeptide having IL-1β activity and a second polypeptide having TNFα activity. Alternatively, the first and second polypeptides have IL-1β and GM-CSF activities, respectively. Preferably, the is a human or livestock animal. The method may further comprise the administration of an antigen such as hereinbefore described or may comprise the administration of a genetic adjuvant or genetic vaccine as described above.

An animal or bird as contemplated by is aspect of the present invention is as hereinbefore defined in relation to the source of cytokine molecules. Where the or bird is to be treated with EL-1β, TNFα or GM-CSF from the same species, this is referred to as a "homologous" system. Where one or more of the cytokines are from a different or bird to the anal or bird being treated, then this is referred to as a "heterologous" system. Both homologous and heterologous systems are contemplated by the present invention.

In an alternative embodiment, the method comprises the sequential administration to said animal or bird of a polypeptide having one of IL-1β activity or TNFα/GM-CSF activity followed by a polypeptide having the other of said IL-1β activity or TNFα/GM-CSF activity.

The polypeptides contemplated above are preferably as hereinbefore defined and include fusion polypeptides.

In a most preferred embodiment, the method contemplated by the present invention comprises administering to an animal (e.g. human or livestock animal) or bird a vaccine composition comprising an antigen, and a first and second polypeptide as contemplated above. The present invention, therefore, is further directed to such a vaccine composition. In a most preferred embodiment, the vaccine composition is a vaccine against nematode infection in livestock animals. The vaccine composition may also be a genetic vaccine comprising one or moire nucleic acid molecules encoding the cytokine or like molecules with or without an antigen and encoded separately or fused together.

The active ingredients of the vaccine composition of the present invention comprising one or more antigens or active immunogenic fragments thereof and an adjuvant composition comprising IL-1β and TNFα or IL-1β and GM-CSF as hereinbefore defined are contemplated to exhibit excellent activity in enhancing an immune response in an animal or bird when administered in an amount which depends on the particular case. The variation depends, for example, on the animal or bird, the antigen and/or the source of first and second polypeptides. For example, from about 0.5 ug to about 20 mg of antigen or combined total of antigen per kilogram of body weight per day may be administered. Furthermore, for 10 μg to 10 mg of IL-1β, TNFα and/or GM-CSF each may be administered per dose. Dosage regime may be adjusted to provide the optimum therapeutic response. For example, several divided doses may be administered daily, weekly, monthly or in other suitable time intervals or the dose may be proportionally reduced as indicated by the exigencies of the situation. The active compound may be administered in a convenient manner such as by the oral, intravenous (where water soluble), intramuscular, subcutaneous, intranasal, intradermal or suppository routes or implanting (e.g. using slow release molecules). Depending on the route of a administration, the active ingredients which comprise one or more antigen and first and second polypeptides as hereinbefore defined may be required to be coated in a material to protect said ingredients from the action of enzymes, acids and other natural conditions which may inactivate said ingredients. For example, the low lipophilicity of the active ingredients may allow them to be destroyed in the gastrointestinal tract by enzymes capable of cleaving peptide bonds and in the stomach by acid hydrolysis. In order to administer the vaccine by other than parenteral administration, the vaccine composition will be coated by, or administered with, a material to prevent its inactivation. For example, the vaccine composition may be co-administered with enzyme inhibitors or in liposomes. The vaccine composition may also contain other compounds such as aluminium hydroxide, resorcinols, non-ionic surfactants such as polyoxyethylene oleyl ether and n-hexadecyl polyethylene ether. Enzyme inhibitors include pancreatic trypsin inhibitor, diisopropylfluorophosphate (DFP) and trasylol. Liposomes include water-in-oil-in-water emulsions as well as conventional liposomes. The vaccine may also comprise Freund's Complete, Freund's Incomplete Adjuvant or aliminum hydroxide.

The active compounds may also be administered in dispersions prepared in glycerol, liquid polyethylene glycols, and/or mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient(s) into a sterile vehicle which contains the basic dispersion medium and the required other ingredients tom those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected as described above, the vaccine may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration the active compound may be incorporated with excipients and used in the form of ingestible tablets, buccal tablets, troches, capsules, elixirs, suspensions, syrups, wafers, and the lie. Such compositions and preparations should contain at least 1% by weight of antigen. The percentage of the compositions and preparations may, of course, be varied and may conveniently be between about 5 to about 80% of the weight of the unit. The amount of active compound in the vaccine compositions is such tat a suitable dosage will be obtained.

The tablets, troches, pills, capsules and the like may also contain the following: a binder such as gum gragacanth acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavoring agent such as peppermint, oil of wintergreen or cherry flavoring. When the dosage unit form is a capsule, it may contain, addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. Where the vaccine is intended for use, the vaccine is conveniently administrable with the animal feed, such as grain. The vaccine composition may also be incorporated into a grain base or may be topically applied to feed grain.

As used herein carriers and/or diluents include any and all solvents, dispersion media, aqueous solutions, coatings, antibacterial and antifungal agents, isotonic and absorption delaying agents, and the like. The use of such media and agents for pharmaceutical active substances is well known in the art. Except insofar as any conventional media or agent is incompatible with the active ingredient, use thereof in the vaccine compositions is contemplated. Supplementary active ingredients can also be incorporated into the compositions. The latter is particularly contemplated as far as the present invention extends to mulitivalent vaccines or multi-component vaccines.

Genetic vaccines may be administered as naked nucleic acid or via viral, insect, bacterial or yeast vectors, or by direct injection into target cells or tissue.

The present invention is further described by reference to the following non-limiting Figures and the Examples.

The following abbreviations are used in the Figure legends and Examples set forth hereinafter:

| | |
|---|---|
| IL-1β | Interleukin-1β |
| TNFα | Tumour Necrosis Factor-α |
| GM-CSF | Granulocyte-Macrophage Colony-Stimulating Factor |
| rOvIL-1β | Recombinant Ovine IL-1β |
| rOvTNFα | Recombinant Ovine TNFα |
| rGM-CSF | Recombinant Ovine GM-CSF |
| AlOH or Alum | Aluminium hydroxide |
| GST | Glutathione-S-transferase |
| 45W | An antigen from *Taenia ovis* |
| GST-45W | Recombinant 45W fused to GST |
| PBS | Phosphate buffered saline |
| IFA | Incomplete Freund's adjuvant |
| i/m | Intramuscularly |
| EIA | Enzyme Immunoassay |
| OD | Optical Density |
| PBST | PBS containing Tween 20 |
| TMB | Tetra-methyl benzidine |
| PHA | Phytohemagglutinin |

| ■ PBS | ▼ PBS + 10ug IL-1 | ✕ PBS + 100ug IL-1 | ● AlOH |
|---|---|---|---|

Figure 8:
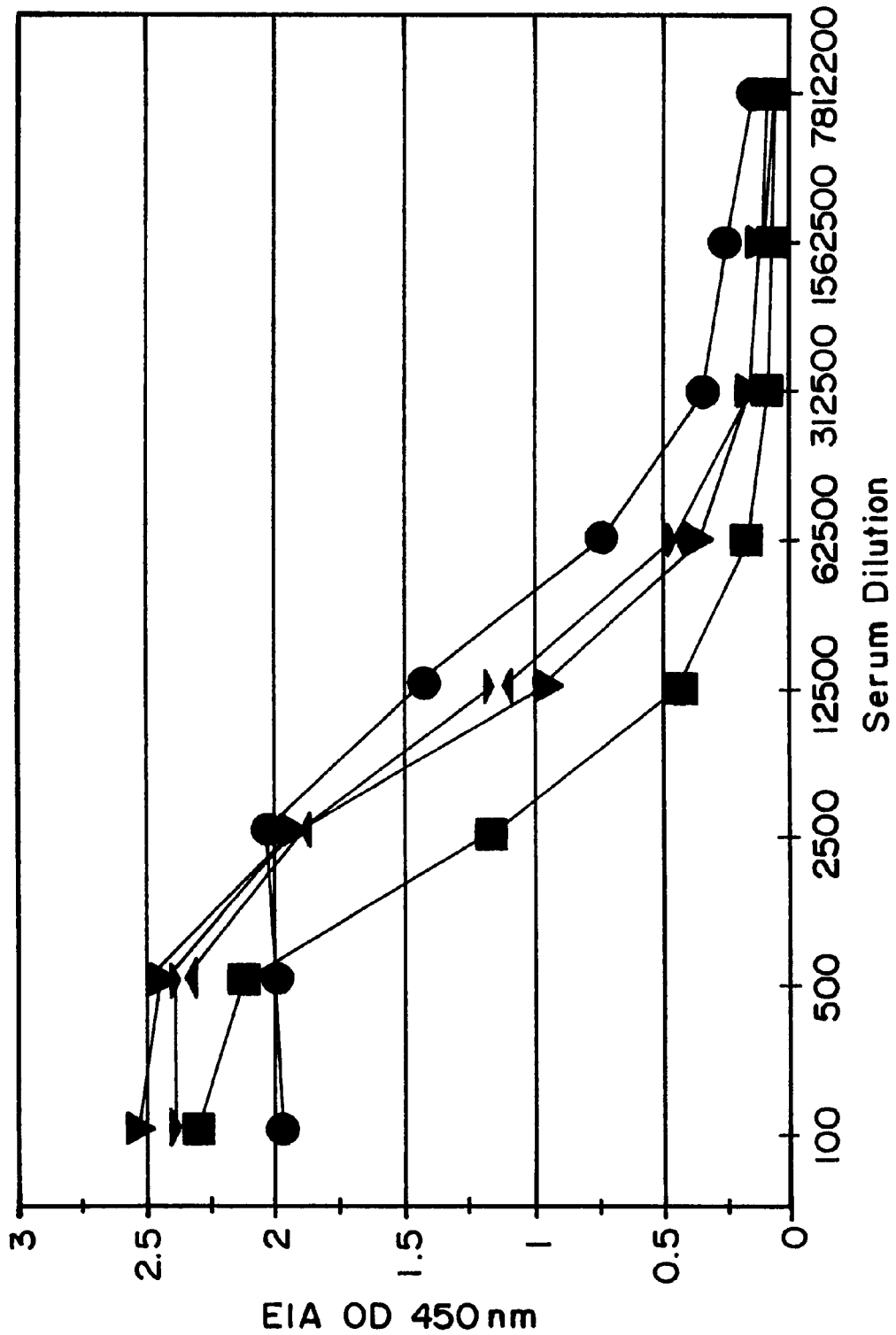

FIG. 8 is a graphical representation showing the adjuvant affect of rOvIL-1β in AlOH 45W vaccine formulations as compared to AlOH alone and Quil A. Sera collected 2 weeks post second vaccination were titrated in an EIA against purified 45W. The results shown are the mean ODs obtained from the 5 sheep per group at each serum dilution.

| ■ AlOH | | ✕ AlOH + 10ug IL-1 |
|---|---|---|
| ▼ AlOH + 100ug IL-1 | ● Quil A | |

Figure 9:
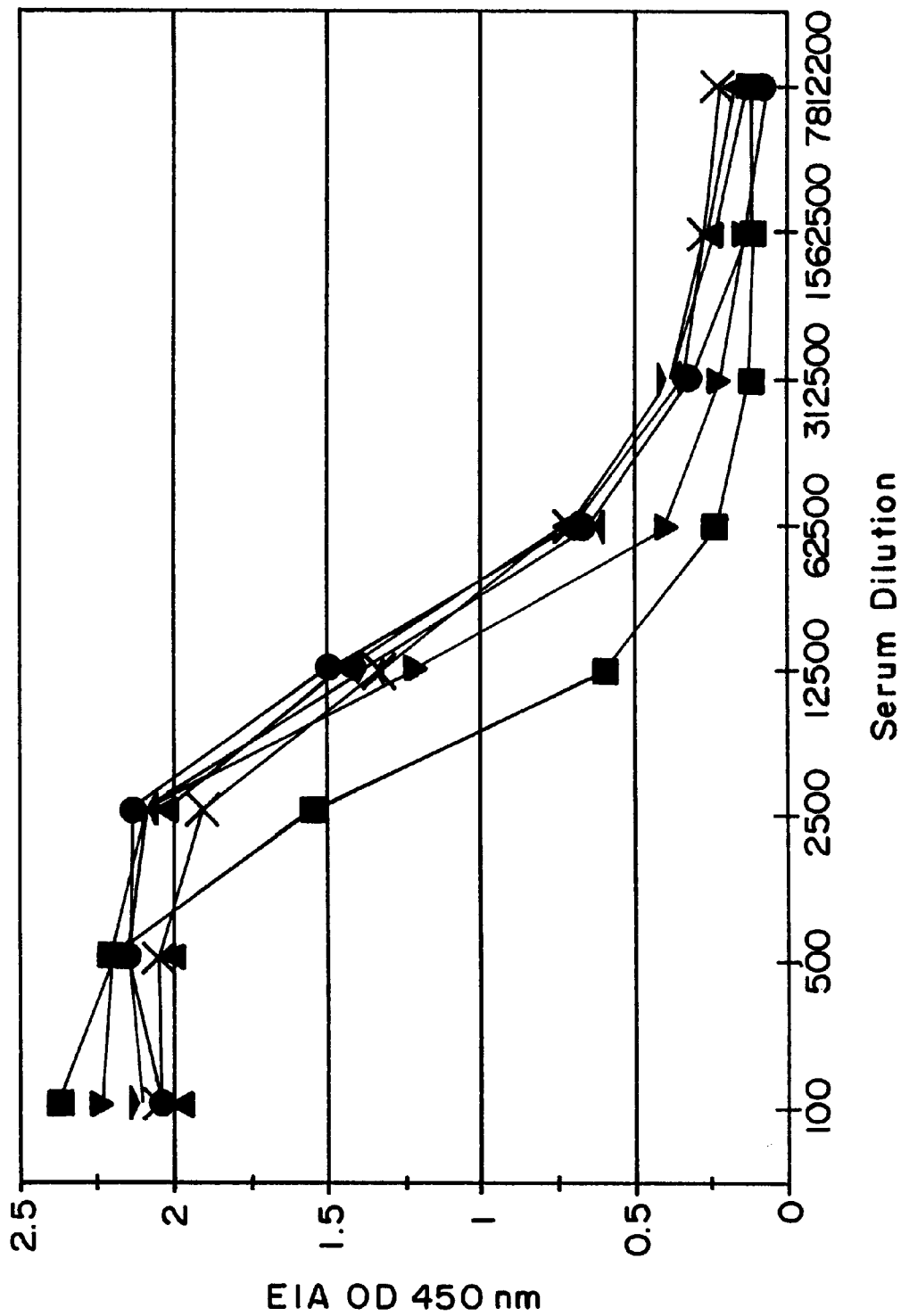

FIG. 9 is a graphical representation showing the adjuvant effect of rOvIL-1β in Quil A and IFA vaccine formulations. Sera collected 2 weeks post second vaccination were titrated in an EIA against purified 45W. The results shown are the mean ODs obtained from the 5 sheep per group at each serum dilution.

| ▼ IFA | ■ IFA + 10ug IL-1 | ✕ IFA + 100ug IL-1 |
|---|---|---|
| ▲ Quil A | ✕ Quil A + 10ug IL-1 | ● Quil A + 100ug IL-1 |

Figure 10:
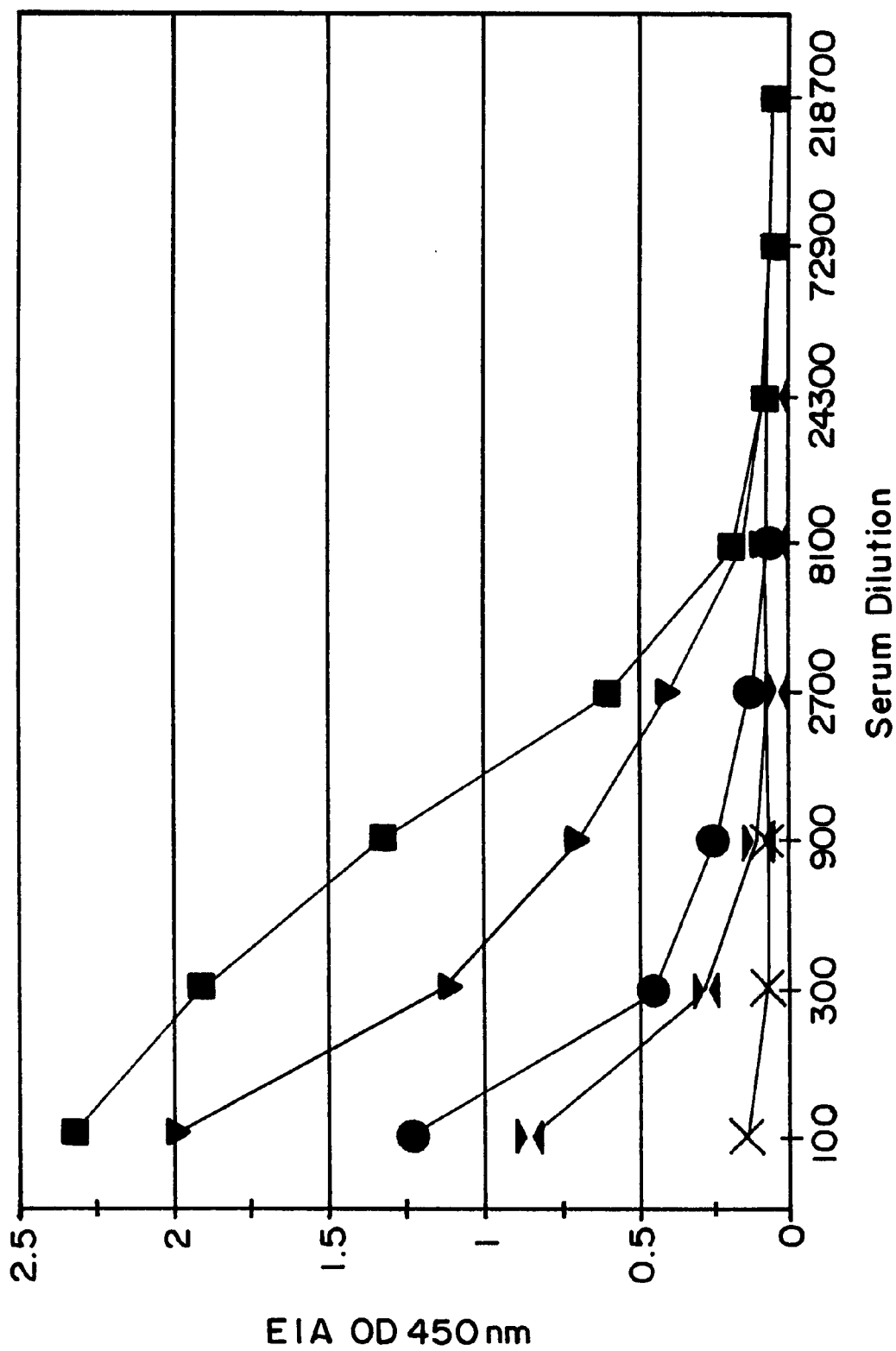

FIG. 10 is a graphical representation showing the adjuvant effect of rOvTNF-α in aqueous 45W vaccine formulations as compared to AlOH and non-vaccinated control sheep. Sera collected 2 weeks post second vaccination were titrated in an EIA against GST-45W. The results shown are the mean ODs obtained from the 5 sheep per group at each serum dilution.

| ✕ PBS | ● PBS + 10ug TNF | ▼ PBS + 100ug TNF |
|---|---|---|
| ■ AlOH | ✕ Controls | |

Figure 11:
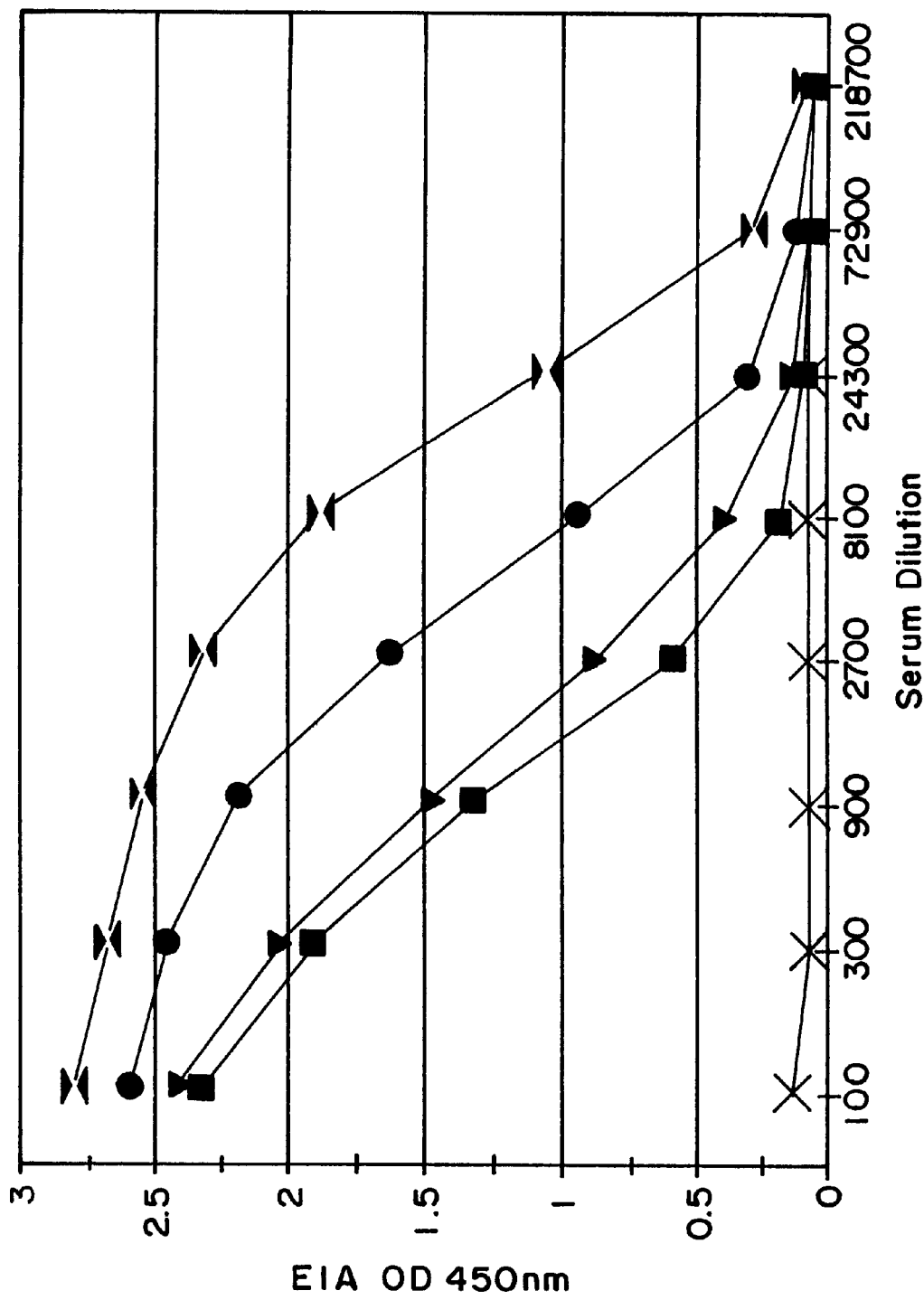

FIG. 11 is a graphical representation showing the adjuvant effect of rOvTNF-α in AlOH 45W vaccine formulations as compared to Quil A and non-vaccinated control sheep. Sera collected 2 weeks post second vaccination were titrated in an EIA against GST-45W. The results shown are the mean ODs obtained from the 5 sheep per group at each serum dilution.

| ■ AlOH | ▼ AlOH + 10ug TNF | ● AlOH + 100ug TNF |
|---|---|---|
| ✕ Quil A | ✕ Controls | |

Figure 12:
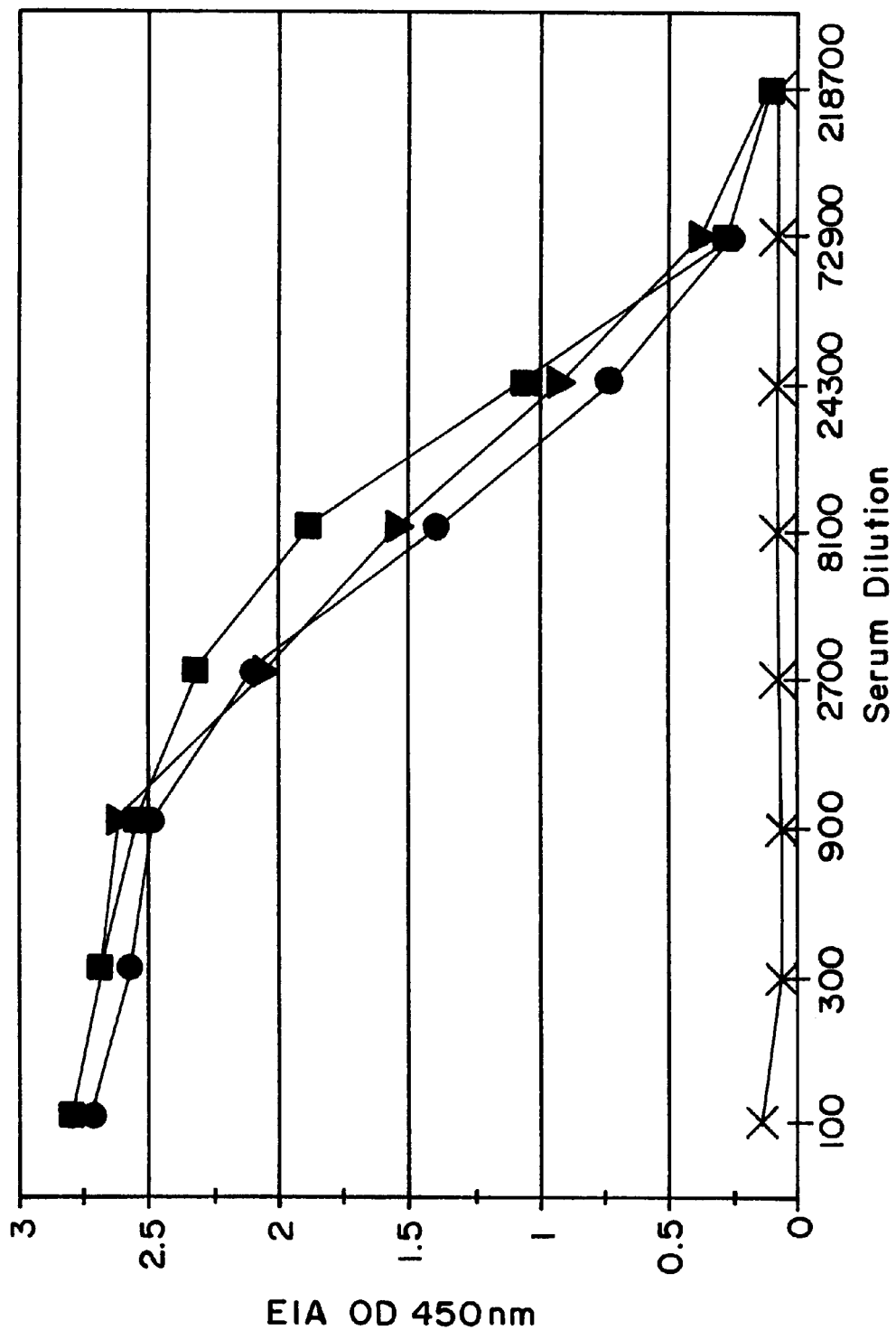

FIG. 12 is a graphical representation showing the adjuvant effect of rOvTNF-α in Quil A 45W vaccine formulations. Sera collected 2 weeks post second vaccination were titrated in an EIA against GST-45W. The results shown are the mean ODs obtained from the 5 sheep per group at each serum dilution.

| ■ Quil A | ● Quil A + 10ug TNF |
|---|---|
| ▼ Quil A + 100ug TNF | ✕ Controls |

Figure 13:
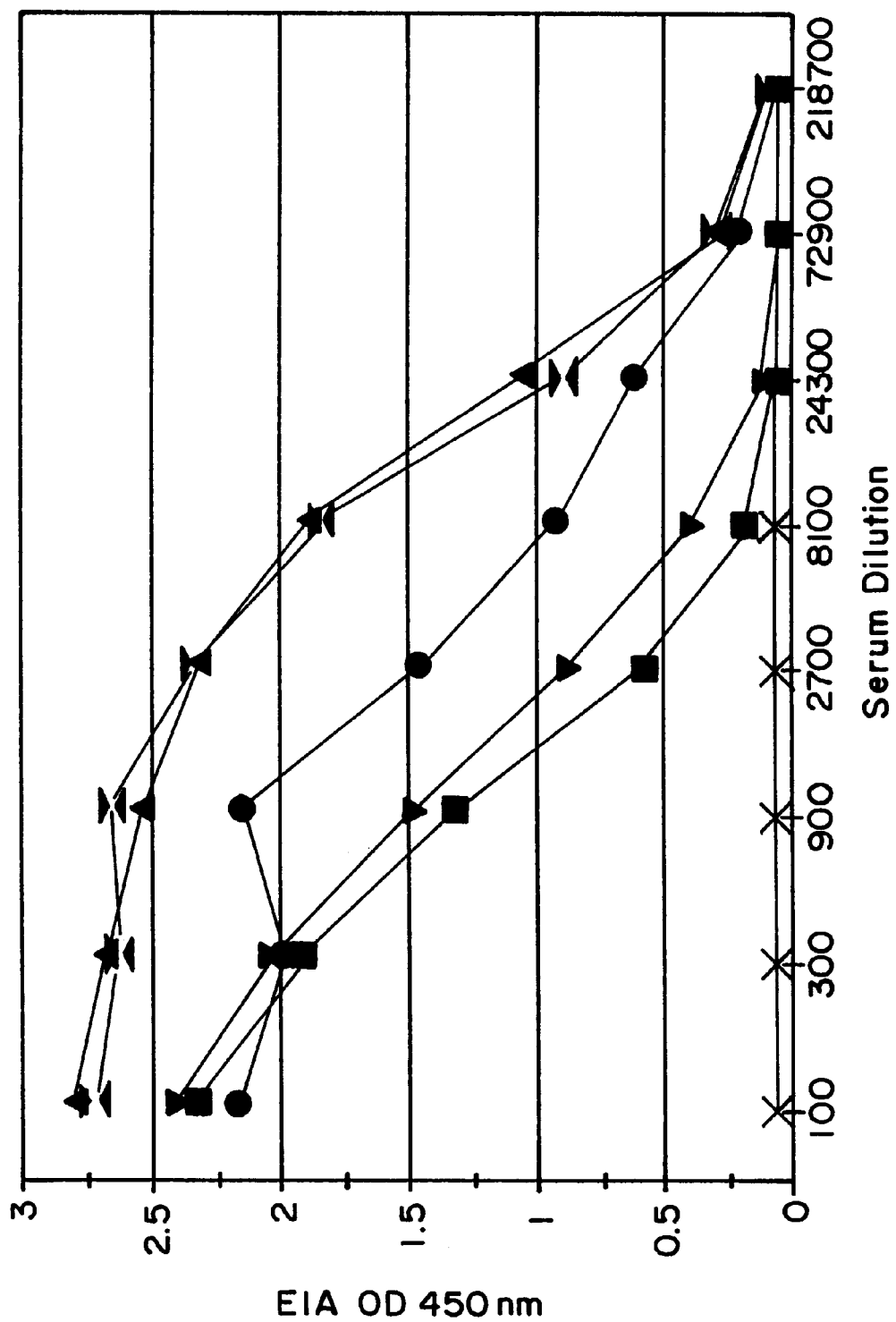

FIG. 13 is a graphical representation showing the adjuvant effect of rOvTNF-α and rOvIL-1β both alone and in combination when incorporated in AlOH 45W vaccine formulations. Antibody responses of non-vaccinated control sheep and those vaccinated with 45W in AlOH alone or Quil A are shown for comparison. Sera collected 2 weeks post second vaccination were titrated in an EIA against GST-45W. The results shown are the mean ODs obtained from the 5 sheep per group at each serum dilution.

| ■ AlOH | ▼ AlOH + 10ug TNF |
|---|---|
| ● AlOH + 10ug IL-1 | ✕ AlOH + 10ug TNF + 10ug IL-1 |
| ▲ Quil A | ✕ Controls |

Figure 14:
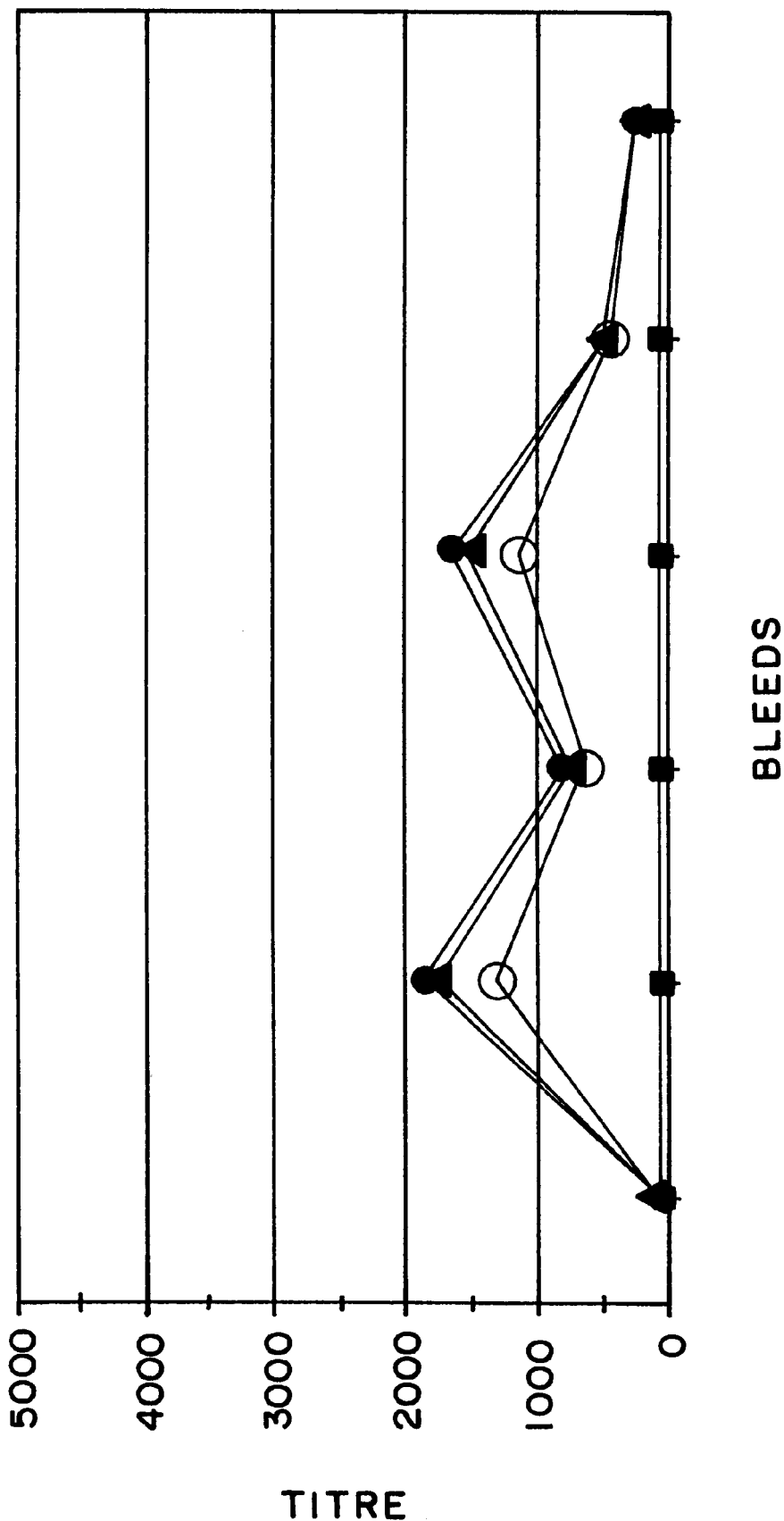

FIG. 14 is a graphical representation showing the antibody titres from sheep vaccinated with the recombinant *Haemonchus contortus* (H.c.) tropomyosin antigen with aluminium hydroxide alone and in combination with either 1 μg/dose or 10 μg/dose of rGM-CSF.

| ■ NIL | ● ALUM + GM(1ug) |
|---|---|
| ▲ ALUM | ⊖ ALUM + GM(10ug) |

Figure 15:
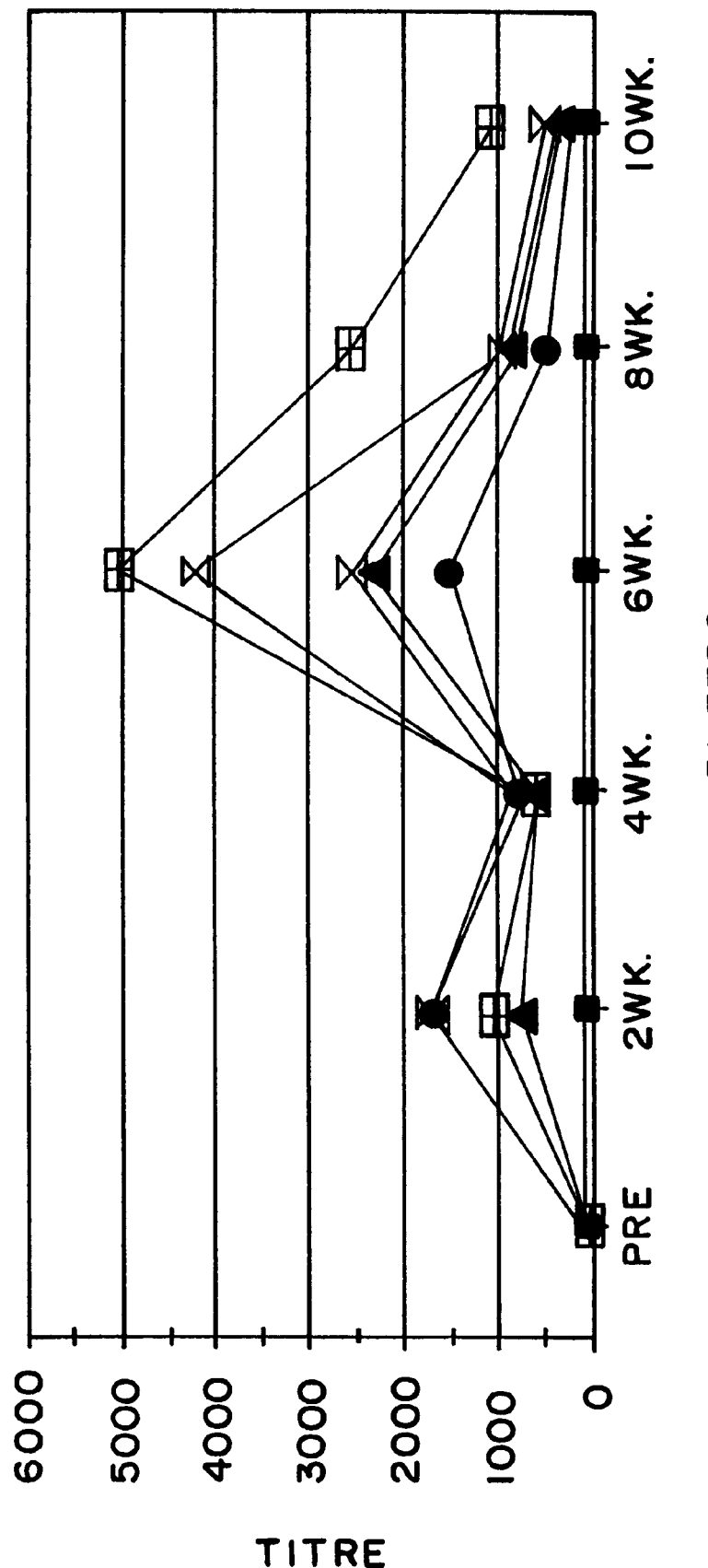

FIG. 15 is a graphical representation showing the titres of antibody over a ten week period.

| ■ NIL | ● ALUM |
|---|---|
| ▲ ALUM + IL-1 + GM(1ug) | ✕ ALUM + IL-1 + GM(10ug) |
| ⊞ GUIL A | ✕ ALUM + IL-1 |

EXAMPLE 1

Animals

Merino wethers, 12–18 months old, were used in subsequent examples to test the efficacy of the vaccine adjuvant.

EXAMPLE 2

Cytokines

Recombinant ovine interleukin-1β (rOvIL-1β) was prepared as described in International Patent Application No. PCT/AU91/00419. Briefly, rOvIL-1β and tumour necrosis factor-α (rOvTNF-α) were prepared as described as follows.

1. Construction of ovine interleukin-1 expression vector

The ovine IL-1β cDNA encoding the mature IL-1β protein was obtained by polymerase chain reaction (PCR) using the following primers:—5'GGATCC GCA GCC GTG CAG TCA 3' (SEQ ID NO. 1) and 5' CCGGTCGAC TAG GGA GAG AGG GGT TCC ATT C 3' (SEQ ID NO. 2). The primers were synthesized with a cohesive BamHI 5' end and a blunt HincII 3' end. The amplified fragment was treated with the Klenow fragment of DNA polymerase I and ligated into the SmaI site of pUC119 and dideoxy sequencing using the T7 polymerase sequencing kit (Pharmacia) was performed to confirm the DNA sequence. The plasmid pUC119 harboring the DNA sequence encoding the mature IL-1β protein was digested with BamHI and HincII. The insert was ligated into the BamHI and SmaI site of the expression vector pGEX-2T (Smith and Johnson, 1988). Transformants of E. coli strain JM109 were produced. The recombinant plasmid was designated pGEX-2T.IL-1β.

2. Expression and affinity purification of recombinant interleukin-1

Overnight cultures of pGEX-2T plasmids were diluted 1:50 in 250 ml of Luria Broth (10 g/L bacto-tryptone, 5 g/L yeast extract, 10 g/L NaCI) or Terrific Broth (16.43 g/L $K_2HPO_4.3H_2O$, 2.31 g/L $KH_2PO_4$, tryptone 12 g/L, yeast 24 g/L, glycerol 4 ml/L) with 100/μg/ml ampicillin. The cultures were grown for 2 h at 37° C. before adding IPTG (isopropyl-β-thiogalactopyranoside) to 0.2 mM (or as indicated in the legend). After 4 h, the cultures were harvested and centrifuged. The pellets were weighed and resuspended in the appropriate volume of buffer (50 m Tris.Cl, pH7.5; 10 ml/g of wet weight of pellet). The cells were lysed on ice by sonication and then centrifuged. The supernatant was loaded onto a 5 ml glutathione Sepharose column (sulphur-linkage, Sigma). The flow through was kept and the column was washed thoroughly with at least 5 bed volumes of 50 mM Tris.CI, pH7.5. The recombinant protein was eluted either as a fusion product with 5 mM glutathione or as free form by cleavage with human thrombin (10 U/ml; ICN) at room temperature for 1 h. The eluted proteins were analysed on a 15% w/v SDS-PAGE (Laemmli, 1970) stained with 0.05% w/v Coomassie Brilliant Blue R.

3. Protein assay concentrations were estimated by the Bradford dye assay (Biorad) using bovine serum albumin as standard.

4. Assay of ovine IL-1β

IL-1β was assayed in two separate bio-assays, 1) thymocyte proliferation in the presence of sub-mitogenic concentrations of lectin and 2) by the ability to stimulate the murine cell line NOB-1 to secrete IL-2 as measured by proliferation of the IL-2 dependent cell line CTLL. Recombinant human IL-1β (National Institute for Biological Standards and Control, Herforshire, England) was used in both assays as a positive control.

For the thymocyte assay, the thymus was aseptically collected from a euthanised lamb (2–8 weeks old). The thymus was then cut into small pieces before being passed through a stainless steel sieve to produce a single cell suspension. The thymocytes were suspended in Dubecco's modification of Eagle's medium (DMEM; Flow Laboratories, Australia) supplemented with 20 mM HEPES, 9 mM sodium bicarbonate, 2 mM L-glutamine, 100 IU/ml penicillin, 100 μg/ml streptomycin and 10% v/v heat-inactivated foetal bovine serum (FBS; Flow Laboratories). After three washes in DMEM, thymocytes were resuspended in DMEM and viable cells counted by trypan blue exclusion. The assay was performed in triplicate in 96-well tissue culture plates with $7 \times 10^5$ thymocytes per well in a total volume of 200 μl per well containing 2 μg/ml of the lectin phytohemagglutinin (PHA) and serial dilutions of IL-1β. Cells were incubated at 37° C., in a humidified atmosphere of 5% $CO_2$ in air, for 72 h before the addition of 3H thymidine (0.5 μCi/well). Cells were harvested 16 h later, using an automated cell harvester, and the amount of $^3H$ thymidine incorporation determined by counting in a Gas proportional β radiation counter.

The NOB-1/CTLL assay was performed as previously described (Gearing et al., 1987) with minor modifications. Briefly, $2 \times 10^5$ NOB-1 cells/well were added in thiplicate to flat-bottomed 96 well tissue culture plates with various dilutions of rOvIL-1β in a total volume of 200 μl/well of DMEM. NOB-1 cells were incubated for 24 h at 37° C. before 50 μl of culture supernatant were transferred to a second 96 well plate along with 100 μl of CTLL cells at a concentration of $4 \times 10^4$ per ml. The CTLL cells were incubated for 20 h at 37° C. before the addition of $^3H$ thymidine (0.5 μCi/well). After a further 3 h incubation, cells were harvested and 3H thymidine incorporation measured as above.

5. Expression and purification of recombinant ovine IL-1β

Figure 1:
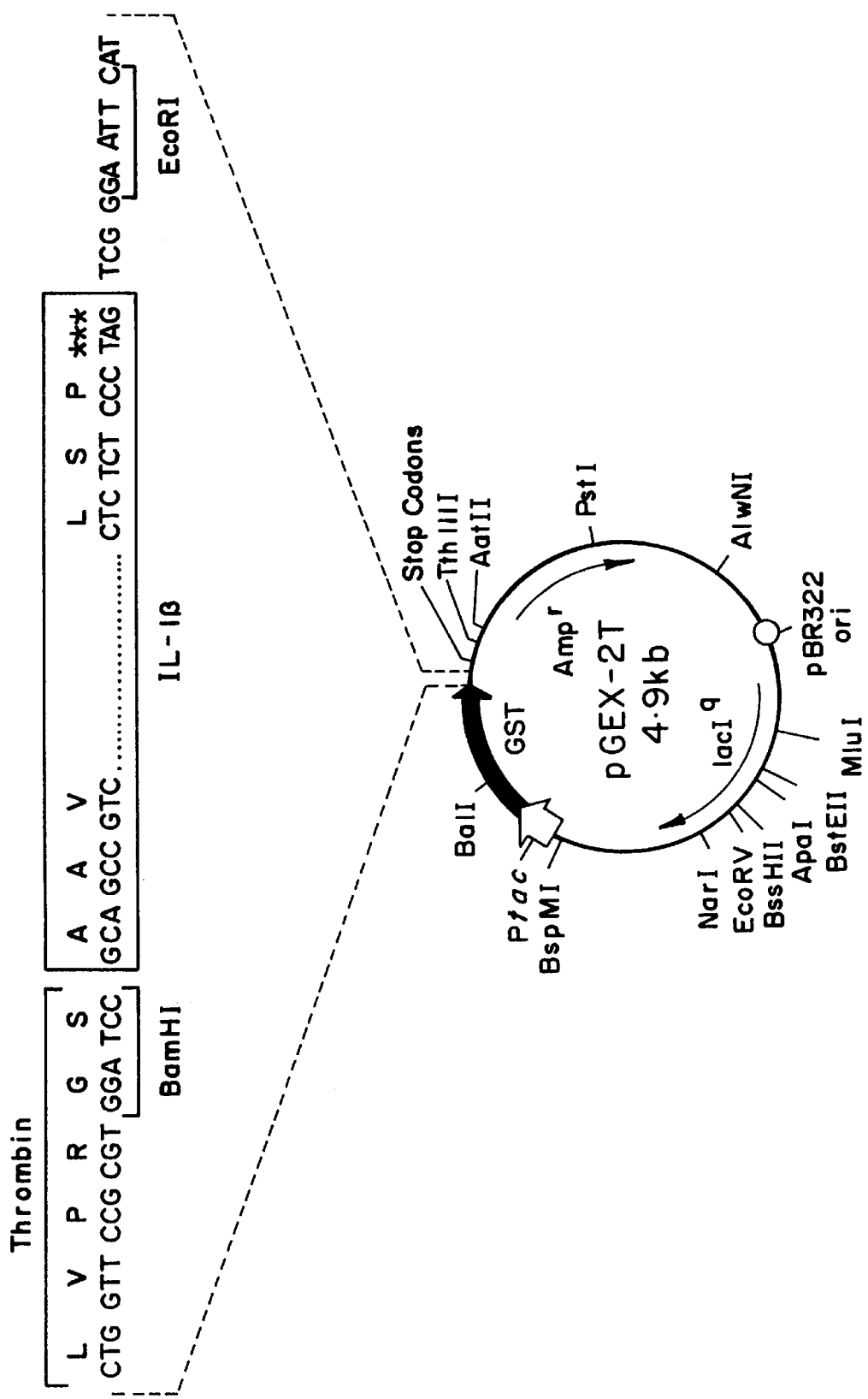
FIG. 1 is a schematic representation of the construction of pGEX-2T.IL-1β expression vector SEQ ID NO: 9 and 10. PCR amplification of plasmid DNA harbourig ovine IL-1β was carried out in a total volume of 100 μl containing 20 ng plasmid DNA, 100 ng of each primer, 200 μM of each dNTPs, 1×Taq polymerase buffer, 1.6 mM MgCl$_2$ and 2.5 U Taq DNA polymerase. The sample was overlaid with 100 μl of mineral oil and subjected to 30 cycles of denaturation at 94° C. for 1 min, annealing at 50° C. for 2 min and extension at 72° C. for 2 min using a DNA thermal cycler. After the final cycle, incubation at 72° C. was continued for 10 min. The PCR product was polished with T4 DNA polymerase I and applied to a 1% w/v agarose gel and purified from the gel slice using a Geneclean kit (BIO 101, USA), ligated to the SmaI site of pUC119 and transformed into JM109. The clones with inserts were sequenced to confirm the IL-1β cDNA sequence encoding the mature protein. The IL-1β DNA insert obtained from the BamHI and HincII digest was ligated into the BamHI and SmaI site of the expression vector, pGEX-2T. This would be in frame with the thrombin cleavage site behind the carboxy terminus of Sj26, a 26 kDa glutathione-S-transferase of the parasite helminth *Schistosoma japonicum*.

The gene encoding the mature form of ovine IL-1β was cloned into the BamHI and SmaI site of the expression plasmid pGEX-2T behind the C-terminus of Sj26, glutaione-S-transferase. FIG. 1 is a schematic illustration of the expression plasmid showing the site of thrombin cleavage of the fusion protein and the restriction sites used to insert the IL-1β gene. Induction of the tac promoter of the expression plasmid pGEX-2T.1L-1β resulted in high level expression of a fusion protein. The recombinant protein was recovered in the soluble fraction and represented approximately 25% of total accumulated proteins as estimated by densitometric scanning of SDS polyacrylamide gels.

Figure 2:
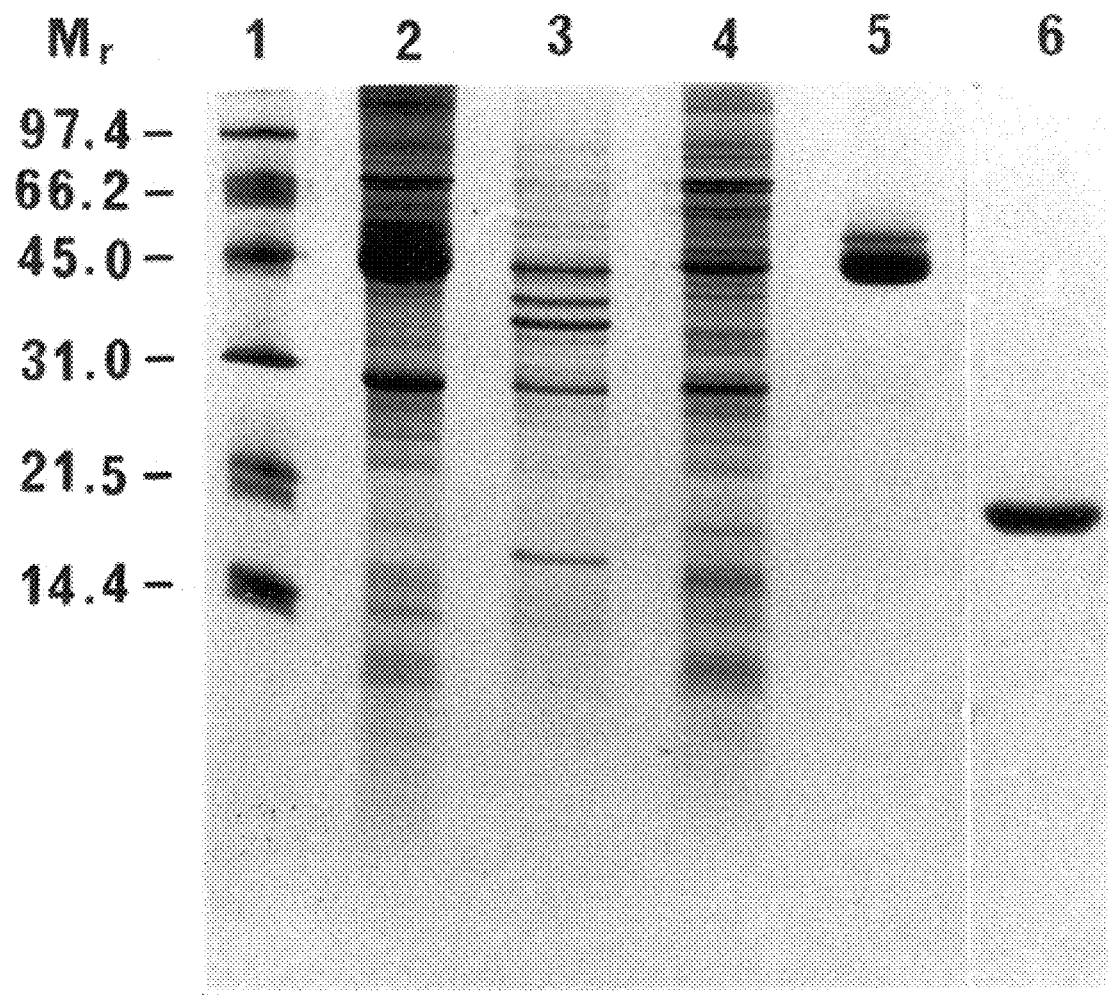
FIG. 2 is a photographic representation of an SDS-PAGE analysis of recombinant ovine IL-1β purified by glutathione Sepharose affinity purification. Lane 1: molecular weight markers (Biorad); lane 2: crude lysate after sonication and loaded onto affinity column; lane 3: insoluble pellet after sonication; lane 4: proteins that did not bind to the column; lane 5: ovine GST-IL-1β fusion protein after glutathione elution; lane 6: ovine IL-1β following thrombin cleavage on the affinity column.

Affinity chromatography of the soluble fraction (FIG. 2, lane 2) on a glutathione-Sepharose column, followed by cleavage with trombin, yielded the free form of mature rOvIL-1β with a molecular weight of approximately 18 kDa (FIG. 2, lane 6). Alternatively, elution from the column with glutathione yielded a fusion protein with a molecular weight of 44 kDa consisting of GST linked to IL-1β (FIG. 2, lane 5). Overall, the amount of rOvIL-1β purified from Luria broth and Terrific broth cultures was 2–3 mg/L and 8–10 mg/L, respectively.

6. Bio-Assay Results

Figure 3:
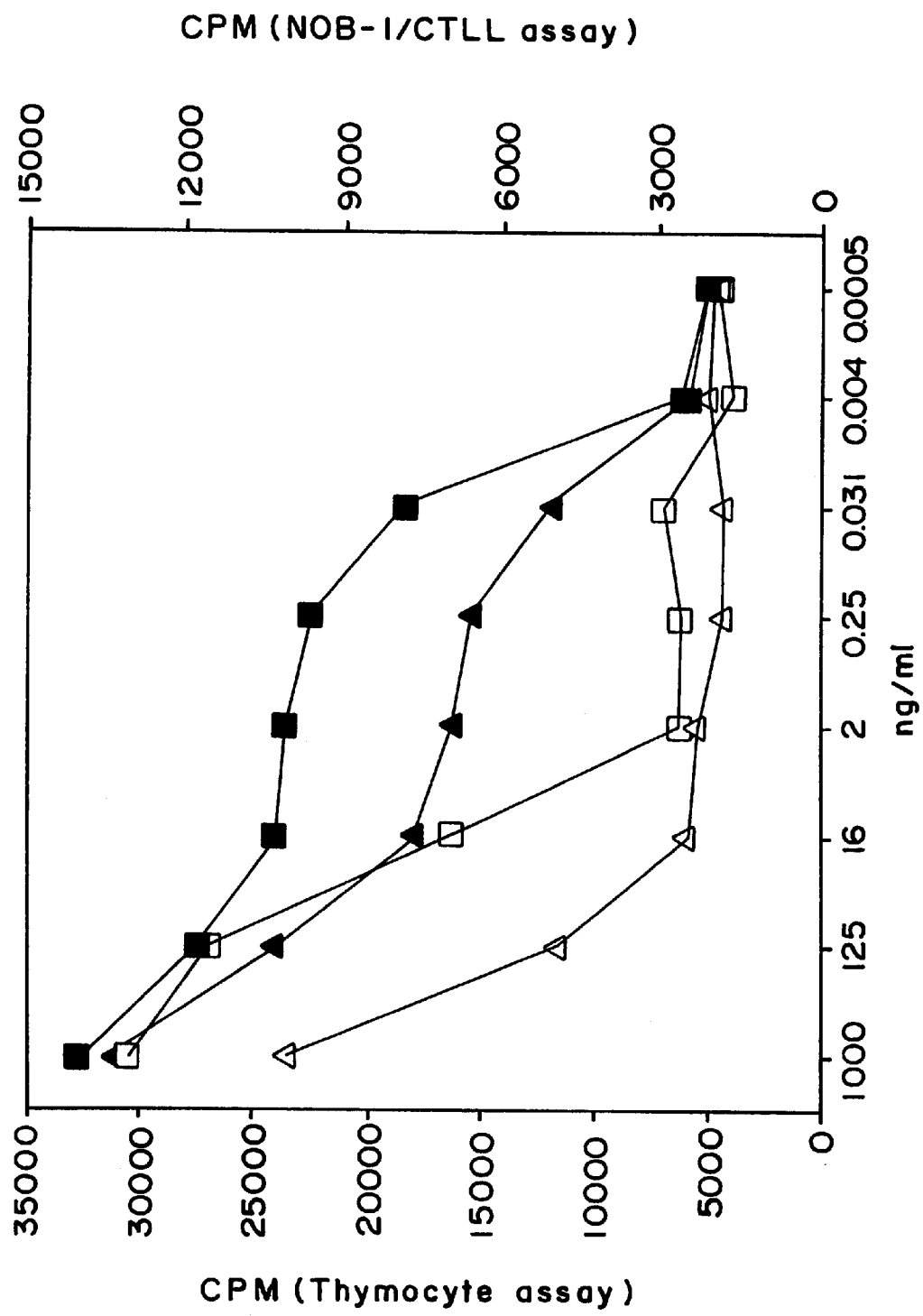
FIG. 3 shows the biological activity of recombinant OvIL-1β preparations in an ovine thymocyte proliferation assay and in the murine NOB-1/CTLL assay. The results shown are mean values from thiplicate wells. Thymocyte assay: ▲, NOB-1/CTLL assay: ■.EL-1 is shown as solid symbols and IL-1-GST as open symbols. Background CPM for unstimulated wells were 1511 and 4396 for the NOB-1/CTLL and thymocyte assays, respectively.
Figure 4:
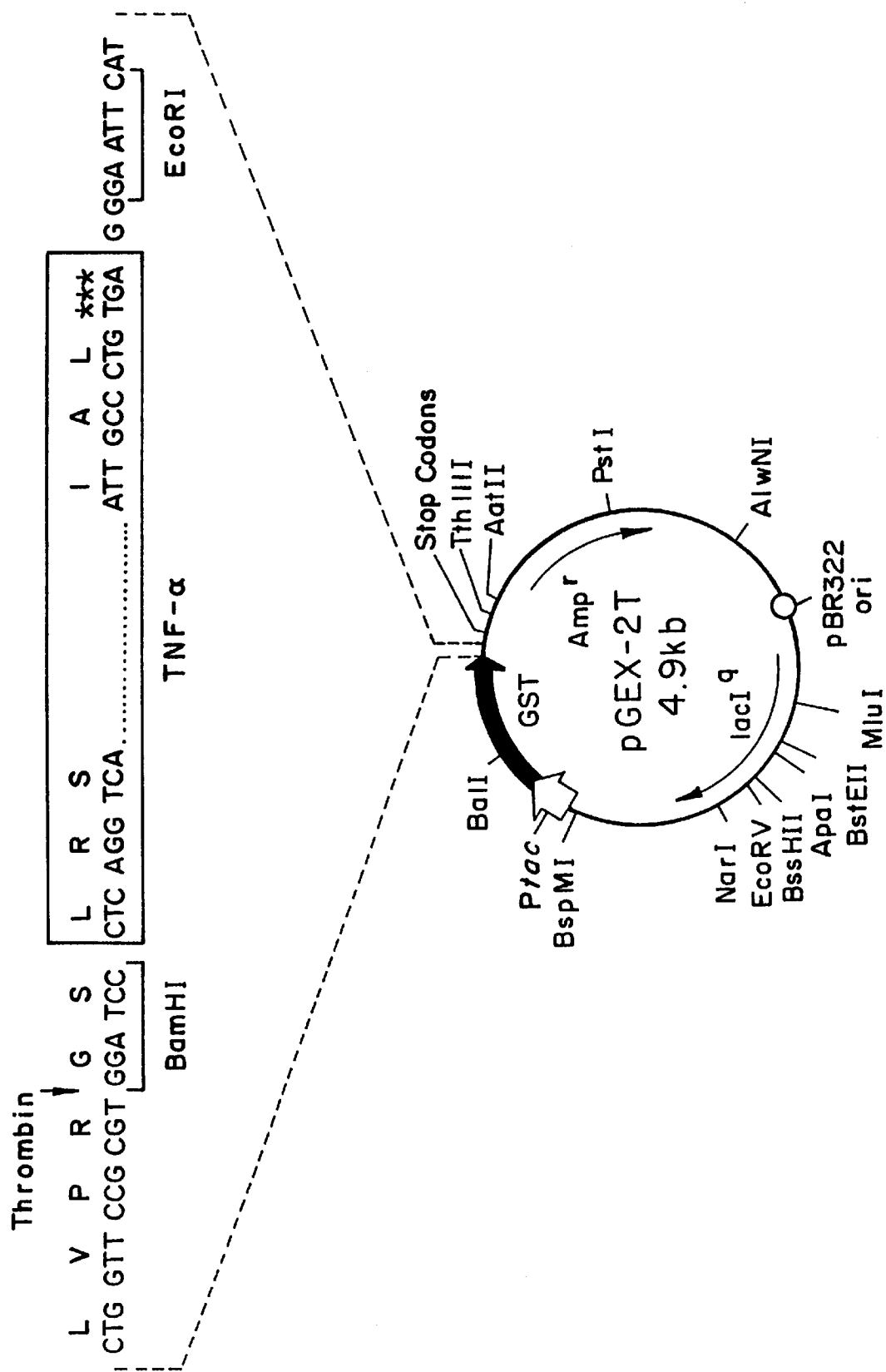
FIG. 4 is a schematic representation of the construction of pGEX-2T.TNFα expression vector SEQ ID NOS: 11 and 12.

Pure and GST fused rOvIL-1β were active in both the thymocyte and the NOB-1/CTLL assays. FIG. 3 shows the activity of both preparations in the thymocyte co-stimulation assay. Specific activities of $5.4 \times 10^3$ U/mg and $5.6 \times 10^7$ U/Mg for GST-IL-1β and IL-1β, respectively, were calculated from the amount of cytokine required to give half-maximal activity in the thymocyte assay. The large increase in specific activity of IL-1β over the GST-IL-1β fusion was also demonstrated in the NOB-1/CTLL may although higher specific activities were obtained; $6.2 \times 10^4$ and $9.1 \times 10^7$ U/mg for GST-IL-1β and IL-1μ respectively (FIG. 4).

4. Construction of TNF expression vector

The ovine TNF-α cDNA encoding the nature TNF-α protein was obtained by PCR using the pUC118-TNF-α DNA as template and the following set of primers: 5' CGCGATCC CTC AGG TCA TCT TCT CAA GCC 3' (SEQ ID NO. 3) (5' BamHI site incorporated) and 5' TCA CAG GGC AAT GAT CCC AAA GTA 3' (SEQ ID NO. 4). PCR amplification of plasmid DNA harbouring ovine TNF-α was carried out. The purified PCR product was ligated into the B and SmaI site of the expression vector, pGEX-2T. This was in frame with the thrombin cleavage site behind the carboxy terminus of Sj26, a 26 kDa glutathione-S-transferase of the parasite helminth Schistosoma japonicum (Smith and Johnson, 1988). The ligated DNA was electroporated into *Escherichia coli* JM109 and the recombinant plasmid designated pGEX2T.TNF-α.

8. Expression and eurification of recombinant ovine TNF

The method used is as described for preparation of recombinant ovine interleukin-1.

9. Assay of recombinant ovine TNF-α

Recombinant ovine TNF-α was assayed by 1) cytotoxcity on L929 cells and 2) ovine thymocyte proliferation in the presence of submitogenic concentrations of lectin. Recombinant human TNF-α ($2.3 \times 10^6$ units/ml) was used in both assays as a positive control.

For the cytotoxicity assay, L929 murine fibroblast cells were added to 96 well culture plates ($2.5 \times 10^5$/well) in Dulbecco's modification of Eagle's medium (DMEM; Flow Laboratories, Australia) supplemented with 20 mM HEPES, 9 mM sodium bicarbonate, 2 mM L-glutamine, 100 lU/ml penicillin, 100 μg/ml streptomycin and 10% v/v heat-inactivated foetal bovine serum (FBS; Flow Laboratories). After 24 hours culture at 37° C. in 5% v/v $CO_2$ the culture media was aspirated and 100 μl of serial dilutions of TNF-α preparations in DMEM containing 1% v/v FBS and 10 μg/ml cycloheximide added to triplicate wells. After a ether 24 hours incubation, culture media was aspirated, plates washed twice with PBS and remaining viable cells stained for 10 minutes with 100 L/well of 0.5% w/v crystal violet in 20% v/v methanol. Plates were then washed extensively with PBS before the addition of 100 μL/well of 33% v/v acetic acid. The solubilized crystal violet was then quantified by measuring the optical density (OD) of each well at 550 nm. The percentage cytolysis was calculated by the formula:

% Cytolysis=(1−(OD test well/OD untreated well))×100

10. Expression and affinity purification of recombinant ovine TNF

Figure 5:
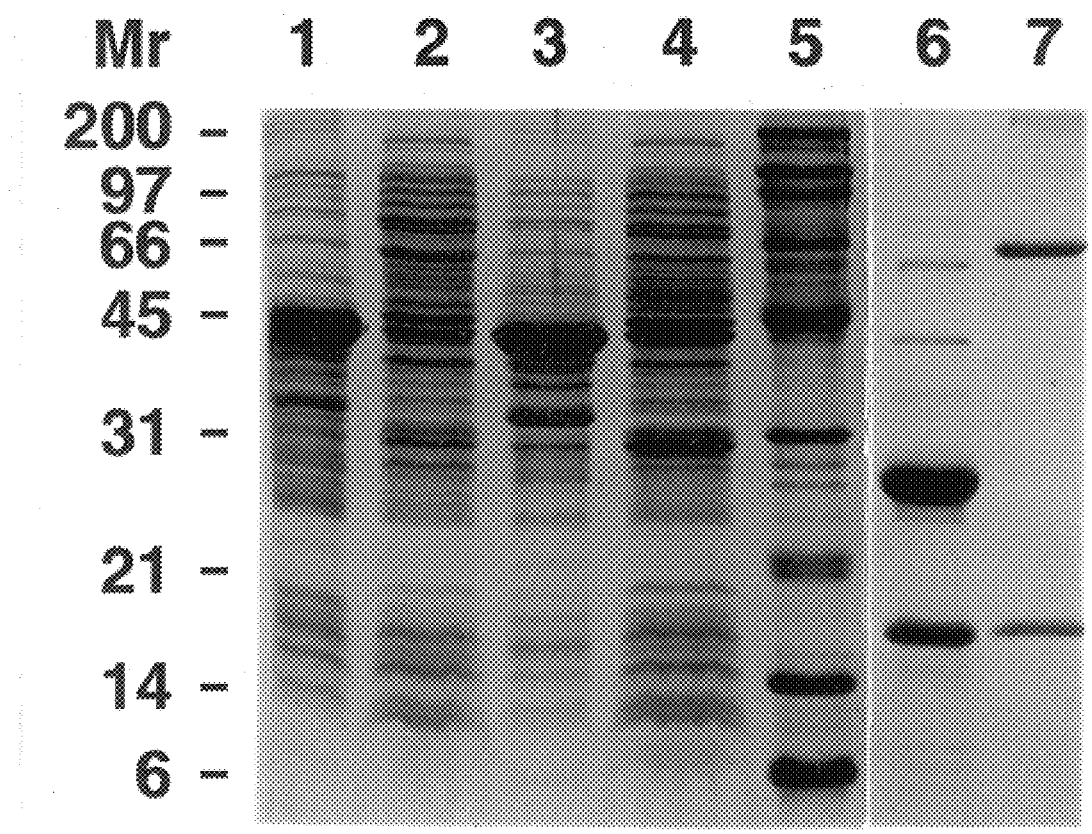
FIG. 5 is an SDS-PAGE analysis of proteins expressed in *E. coli* strain JM109. Lane 1: proteins in the insoluble fraction from growth at 37° C. Lane 2: Soluble fraction from growth at 37° C. Total accumulated proteins at 30° C. and the corresponding insoluble fraction (lane 3) and soluble fraction (lane 4). Lane 5: Molecular weight markers (BioRad). Lane 6: Fusion protein cleaved with thrombin to yield GST and rOvTNF. Line 7: purified rOvTNF with carrier protein BSA (0.2% w/v) added.

FIG. 4 is a schematic representation of the expression constuct showing the site of thrombin cleavage of the fusion protein and restriction enzyme sites used to clone the OvTNF-α gene encoding the mature protein. Induction of the tac promoter resulted in expression of a fusion protein of approximately 43 kDa as shown by SDS-PAGE analysis (FIG. 5). The amount of recombinant protein in the soluble fraction was only 5.3% of total proteins as estimated by densitometric scanning of the COmassie-blue stained gel (FIG. 5, lane 2). When the growth temperature was lowered to 30° C. The level of expression of soluble recombinant product was increased to 8.6% (FIG. 5, lane 4).

Elution of the bound protein with glutathione yielded a fusion protein of 43 kDa. Thrombin digestion of the fusion protein was performed following elution of the fusion protein with glutathione. This gave rise to GST of 26 kDa and the rOvTNF-α of 17 kDa (FIG. 5, lane 6). The GST moiety was rebound on the glutathione affinity column leaving the rOvTNF-α in the flowthrough. BSA was added to the purified rOvTNF-α as carrier (FIG. 5, lane 7).

11. Bio-assay

Figure 6:
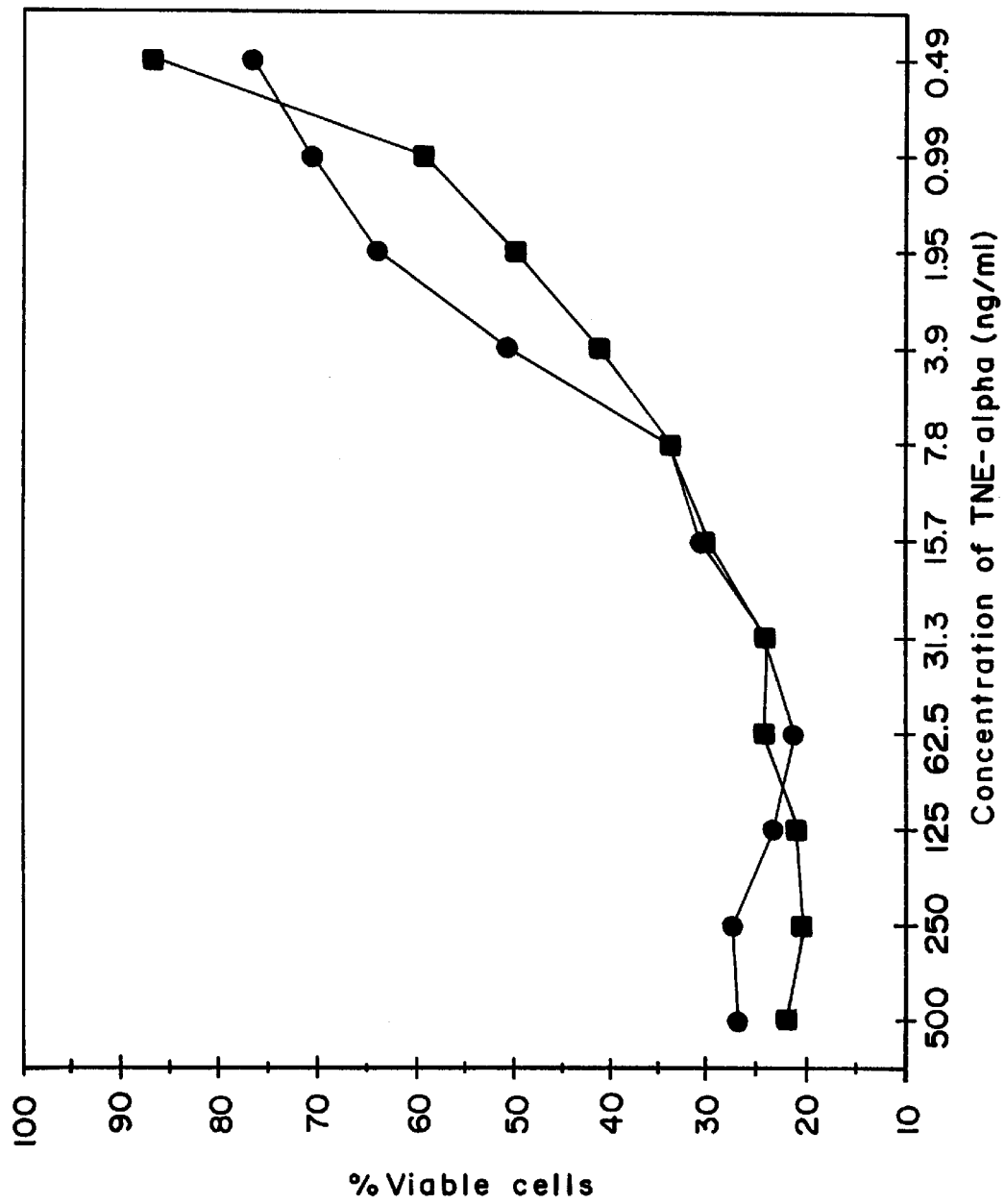
FIG. 6 is a graphical representation showing the cytotoxic effect of recombinant ovine (■) and human (●) TNF-α on murine L929 cells.

Recombinant ovine and human TNF-α demonstrated similar levels of activity in the L929 assay (FIG. 6). In repeated assays, both TNF-α preparations routinely generated 50% cytotoxicity for L929 cells at concentrations of approximately 1 ng/ml. This equates to a biological activity of $1 \times 10^6$ units per mi which is win assay variability of at quoted for the human preparation. The rOvTNF-α GST fusion protein exhibited the same activity in the L929 assay as the purified protein.

Before use in vivo, the purified cytokines were passed through a Detoxi column (Pierce) to remove the possibility of endotoxin contamination.

Recombinant ovine IL-1β was expressed and purified as previously described (Seow et al, 1994). rGM-CSF was obtained from a Chinese hamster ovary cell expression system and its specific activity was determined from a liquid proliferation assay using bone marrow cells.

EXAMPLE 3

Vaccine Preparations

The recombinant *Taenia ovis* fusion protein GST-45W (Johnson et al., 1989) was used as the model antigen in all studies. Vaccines were formulated with 50 μkg/dose of GST-45W and 0, 10 or 100 μg/dose of IL-1β and/or TNF-α in either phosphate buffered saline (PBS) or the conventional adjuvants Quil A (1 or 5 mg/ml), incomplete Freund's adjuvant (IFA; 1:1, oil:water) and aluminium hydoxide (6 mg/ml). Sheep were injected intra muscularly (i/m) (1 ml) into the left hind leg for the primary inoculation and 4 weeks later boosted with an i/m injection of the same vaccine preparation into the right hind leg.

EXAMPLE 4

Serology

Serum examples were collected from all animals before the primary inoculations and then at weekly intervals until 4 weeks post secondary inoculation. Sera was stored at −20° C. until assayed for antibodies to 45W using the enzyme immunoassay (EIA) described below. Pre-bleed sera from all sheep was screened for antibodies to 45W prior to the commencement of experiments and any animals demonstrating significant antibody levels to 45W (EIA OD>0.2 at 1/300 ser dilution) were excluded. For the EIA, either recombinant 45W, thrombin cleaved and purified from the GST moiety or GST-45W (as indicated), was bound to 96-well microtitre plates (Nunc Maxisorb) by incubating 0.2 μg per well in 100 μl of 50 mM carbonate buffer (pH 9.6) for 20 hrs at 20° C. The plates were then post-coated (1 hr at 20° C.) with 100 μl per well of phosphate buffered saline (PBS: 0.9% w/v, pH 7.2) containing 1% w/v sodium casein. After 4 washes with phosphate buffered saline containing 0.05% v/v Tween 20 (PBST), 100 μl of serial dilutions of serum samples were added to the wells for 1 hr at 20° C. The plate were then washed 4 times with PBST before the addition of 100 μl per well of a 1/1000 dilation of horseradish peroxidase conjugated anti-ovine IgG monoclonal antibody (VET05, Silenus, Australia) in PBST for 1 hr at 20° C. Plates were washed 5 times with PBST and 100 μl of tetra-methyl benzidine (TMB) substrate (Bos et at, 1981) added to each well for 30 min at 20° C. before the reaction was stopped by the addition of 50 μl of 0.5M $H_2SO_4$ per well and the absorbance read at 450 mm.

EXAMPLE 5

Adjuvant Activity of rOvIL-1β

Figure 7:
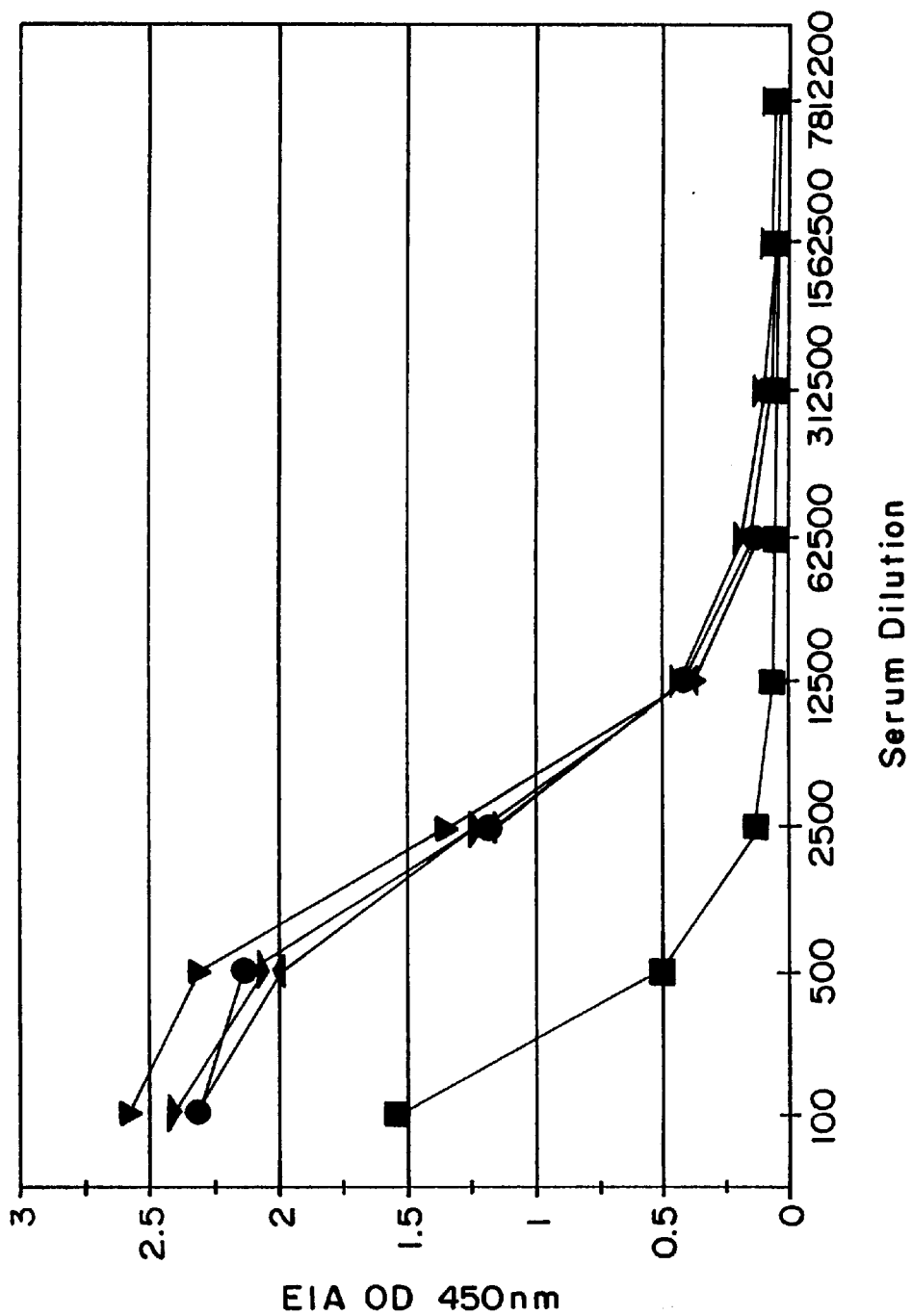
FIG. 7 is a graphical representation showing the adjuvant effect of rOvIL-1β in aqueous 45W vaccine formulations as compared to AlOH. Sera collected 2 weeks post second vaccination were titrated in an EIA against purified 45W. The results shown are the mean ODs obtained from the 5 sheep per group at each serum dilution.

Sheep were randomly allocated into 12 groups of 5 as detailed in Table 2. Serum samples were collected prior to first vaccination and then at weekly intervals until 4 weeks post secondary vaccination. Serum antibody levels to purified 45W were quantified by EIA. All vaccine formulations contained 50 μg of GST-45W per dose. The addition of either 10 or 100 μg of rOvIL-1β to the aqueous (PBS; FIG. 7) and AlOH (FIG. 8) vaccine formulations resulted in significant increases in serum IgG anti-45W. Both concentrations of rOvIL-1β tested stimulated antibody production to the same extent. The incorporation of rOvIL-1β in the Quil A (5 mg/dose) and IFA formulations did not further enhance the antibody levels elicited (FIG. 9).

EXAMPLE 6

Adjuvant Activity of rOvTNF-α

An experiment similar to that described in Example 5 for rOvIL-β was conducted with rOvTNF-α to ascertain its adjuvant potential. The vaccine preparations for is experiment are listed in Table 3. Serum antibody levels were quantified by ERA using GST-45W antigen. As in Example 5, adjuvant effects were seen in the PBS (FIG. 10) and AlOH (FIG. 11) vaccine groups when either 10 or 100 μg of rOvTNF-α were incorporated. Recombinant OvTNF-α alone as adjuvant was sufficient to induce antibody production with the 100 μg dose being more effective than 10 μg. There was no enhancement of antibody titre in the Quil A groups when rOvTNF-α was added (FIG. 12).

EXAMPLE 7

Adjuvant Activity of rOvIL-1β and rOvTNF-α in Combination

The combination of 10 μg of both IL-1β and TNF-α was studied in AlOH vaccine formulations. Table 4 shows the vaccine groups, and the antibody titres to GST-45W, at two weeks post second vaccination, are shown in FIG. 13. The two cytokines exerted synergistic co-adjuvant effects when administered with AlOH which resulted in a>15 fold increase in antibody titre compared to that obtained when AlOH alone was used as adjuvant (FIG. 13). The level of antibody obtained with the AlOH-cytokine combination was commensurate with that obtained with Quil A.

TABLE 2 rOvIL-β Vaccine Preparations

| VACCINE FORMULATION | μg of rOvIL-1β |
|---|---|
| 1/PBS | 0 |
| 2/ PBS | 10 |
| 3/ PBS | 100 |
| 4/ QUIL A (5 mg/dose) | 0 |
| 5/ QUIL A (5 mg/dose) | 10 |
| 6/ QUIL A (5 mg/dose) | 100 |
| 7/ IFA (Oil:H₂O, 1:1) | 0 |
| 8/ IFA (Oil:H₂O, 1:1) | 10 |
| 9/ IFA (Oil:H₂O, 1:1) | 100 |
| 10/ AlOH (6 mg/dose) | 0 |
| 11/ AlOH (6 mg/dose) | 10 |
| 12/ AlOH (6 mg/dose) | 100 |

All vaccine preparations were formulated to a volume of 1 ml per dose containing 50 μg of GST-45W fusion protein. There were 5 sheep per vaccine group. Animals were injected i/m in the left rear leg on day 0 and received a second i/m injection in the right leg on day 28.

TABLE 3 rOvTNF-α vaccine preparations

| VACCINE FORMULATION | μg of rOvTNF-α |
|---|---|
| 1/ PBS | 0 |
| 2/ PBS | 10 |
| 3/ PBS | 100 |
| 4/ QUIL A (1 mg/dose) | 0 |
| 5/ QUIL A (1 mg/dose) | 10 |
| 6/ QUIL A (1 mg/dose) | 100 |
| 7/ AlOH (6 mg/dose) | 0 |
| 8/ AlOH (6 mg/dose) | 10 |
| 9/ AlOH (6 mg(dose) | 100 |
| 10/ Controls (no vaccine) | |

All vaccine preparations were formulated to a volume of 1 ml per dose containing 50 μg of GST-45W fusion protein. There were 5 sheep per group. Animals were injected i/m in the left rear leg on day 0 and received a second i/m injection in the right rear leg on day 28.

TABLE 4

Combined rOvTNF-α and rOvILβ vaccine preparations

| VACCINE FORMULATION | μg of rOvTNF-α | μg of rOvIL-1β |
|---|---|---|
| 1/ AlOH (6 mg/dose) | 0 | 0 |
| 2/ AlOH (6 mg/dose) | 10 | 0 |
| 3/ AlOH (6 mg/dose) | 0 | 10 |
| 4/ AlOH (6 mg/dose) | 10 | 10 |
| 5/ QUIL A (1 mg/dose) | 0 | 0 |
| 6/ Controls (no vaccine) | | |

All vaccine preparations were formulated to a volume of 1 ml per dose containing 50 μg of GST-45W fusion protein. There were 5 sheep per group. Animals were injected i/m in the left rear leg on day 0 and received a second i/m injection in the right rear leg on day 28.

EXAMPLE 8

Adjuvant Activity of rOvIL-1β and rOvGM-CSF

This example shows the ability of ovine IL-1β and ovine GM-CSF to boost antibody levels to the protective H.C. antigen tropomyosin in the presence of the conventional adjuvant AlOH₃. The results are shown in Table 5 and FIGS. 14 and 15.

TABLE 5

| Vaccine formulation | μg of rOvIL-1β | μg of rOvGM-CSF |
|---|---|---|
| 1. Nil | 0 | 0 |
| 2. Al(OH)₃ (6 mg/dose) | 0 | 0 |
| 3. M(OH)₃ | 10 | 0 |
| 4. Al(OH)₃ | 0 | 1 |
| 5. Al(OH)₃ | 0 | 10 |
| 6. Al(OH)₃ | 10 | 1 |
| 7. Al(OH)₃ | 10 | 10 |
| 8. QuilA (1 mg/dose) | 0 | 0 |

Table 5 shows the various formulations used. Each group consisted of 5 sheep. Vaccines were formulated with 50 μg/dose of recombinant *Haemonchus contortus* tropomyosin antigen and aluminium hydroxide with 10 μg/dose of IL-1β and/or 10 μg/dose of GM-CSF. Another group of 5 sheep were vaccinated with the same antigen with either Quil A or aluminium hydroxide. Sheep were injected subcutaneously into the right hind leg for primary inoculation and 4 weeks later boosted with another subcutaneous injection of the same vaccine preparation. Blood was collected from all animals just before the primary inoculation and then fortnightly until week 10. The sera were stored at −20° C. until all sera was collected. The titre of antibodies to tropomyosin (41 kDa) was measured using standard enzyme immunoassay (EIA).

FIG. 14 is a graphical representation showing the antibody titres from sheep vaccinated with the recombinant *Haemonchus contortus* (H.c.) tropomyosin antigen with aluminium hydroxide alone and in combination with either 1 μg/dose or 10 μg/dose of rGM-CSF.

FIG. 15 is a graphical representation showing the mean titres of antibody over the ten week period. The highest amount of antibody was detected at week 6 post primary inoculation in all the groups. FIG. 15 was generated using data from only 4 animals in the aluminum hydroxide +IL-1β+GM-CSF (10 μg) vaccination group as one animal failed to respond to the booster vaccination. However, statistical analysis was done on data from all 5 animals and therefore the results of the analysis are conservative. The difference in mean titres at this time were significantly difference $F_{(5,24)}$= 43.5, p<0.0001) and the treatments formed three distinct clusters that are significantly different from each other (Tukey HSD); cluster 1—the nil treatment; cluster 2—aluminium hydroxide, aluminium hydroxide+IL-1β and aluminium hydroxide+IL-1β+GM-CSF (1 μg), and cluster 3'aluminium hydroxide+IL-1β+GM-CSF (10 μg) and Quil A. The addition of the IL-1β to aluminium hydroxide enhanced mean antibody titre by 1.7 fold compared to alaminnun hydroxide alone. The combination of IL-1β and GM-CSF (1 μg) added to aliminum hydroxide increased the mean time 1.3 fold over aliminum hydoxide alone. At this time the combination of IL-1β and GM-CSF (10 μg) added to aluminium hydroxide increased the mean titre 2.3 fold over aluminium hydroxide alone. Quil A was the most effective adjuvant with the meam titre 4.9 fold higher than aluminium hydroxide. It has been previously shown with other antigens that IL-1β can act as an adjuvant. This is the first demonstration that the combination of IL-1β and GM-CSF with aluminium hydroxide was a better adjuvant than aluminium hydroxide alone. The antibody titre with the combination of IL-1β and GM-CSF was lower than with Quil A.

Those skilled in the art will appreciate that the invention described herein is susceptible to variations and modifications other than those specifically describe. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Anderson, G., Urban, O., Fedorka-Cray, P., et al. 1987. Interleukin-2 and protective immunity in *Haemophilus pleuropneumoniae*: preliminary studies. pp 22–25 In: Vaccines 87. Chanock R. M., Lerner, R. A., Brown, F., Ginsberg, H. (ed). Modern Approaches to New Vaccines: Prevention of AIDS and Other Viral Bacterial and Parasitic Disease. Cold Spring Harbour Laboratory, Cold Spring Harbour, N.Y.

Balkwill, F. R. and Burke, F. 1989. *Immunol Today* 9: 299.

Blecha, F. 1990. Immunomodulation in domestic food animals. In: Advances in veterinary science and comparative medicine. Blecha and Charley Eds. pp. 231–254. Academic press, London.

Bos, E. S., van der Doelen, A. A., van Rooy, N. and Schuurs, A. H. W. M., 1981. *J. Immunoassay.* 2: 187–204.

Cox, J. C. and Coulter, A. R. 1992. In: Animal Parasite Control Utilizing Biotechnology. Yong, W. K. (Ed). pp 79. CRC Press, Boca Ranton, Fla. U.S.A.

Clutterbuck, E. J., Hirst E. M. A. and Sanderson, C. J. 1989. *Blood* 73: 1504–1512.

East, I. J. 1993. Adjuvants for New Veterinary Vaccines. In: Progess in Vaccinology. 4. Veterinary Vaccines. Pandey, R., Hoglund, S. and Prasad, G. Eds. pp. 1–28. Springer-Verlag.

Gearing, A. J. H., Bird, C. R., Bristow, A., Poole, S. and Thorpe, R., 1987. *J. Immunol.* 99: 7–11.

Ghiara, P., Boraschi, D., Nencioni, L., Ghezzi, P., and Tagliabue, A. 1987. *J. Immunol.* 139: 3676–3679.

Good, M. F. 1988. *J. Immunol.* 141: 972.

Heath, A. W. and Playdair, J. H. L. 1992. *Vaccine* 10: 427–434.

Johnson, K. S., Harrison, G. B. L., Lightowlers, M. W., P'Hoy, K. L., Cougle, W. G., Dempster, R. P., Lawrence, S. B., Vinton, J. G., Heath, D. D. and Rickard, M. D. 1989. *Nature.* 338: 585–587.

Kawahima, K., and Platt, K. B. 1989. *Vet. Immunol. Immunopathol.* 22: 345.

Laemmli, U. K., 1970. *Nature,* 227: 680–685.

Maniatis, T., Fritsch, E. F. and Sambrook, J. 1982. Molecular Cloning: A Laboratory Manual. Cold Spring Harbor Laboratory, Cold Spring Harbor, N.Y., 1982.

Merrifield. 1964. *J. Am. Chem. Soc.* 85: 2149.

Nash, A. D. Lofthouse, S. A., Barchan, G. J., Jacobs, H. J., Ashman, K., Meeusen, E. N. T., Brandon, M. R. and Andrews, A. E. 1993. *Immunol. Cell Biol.* 71: 367–379.

Nunberg, J. H., Doyle, M. V., Newell, A. D., Anderson, G. A. and York, C J. 1988. Interleukin 2 as an adjuvant to vaccination. In: H. Gunsberg at al. Eds, Vaccines 88. New chemical and genetic approaches to vaccination. Cold Spring Harbour, N.Y.

Nunberg, J. H., Doyle, M. V., York, S. M., York, C. J. 1989. *Poc. Natl. Acad. Sci. U.S.A.* 86: 4240–4243.

Playfair, J. H. L. and de Souza J. B. 1987. *Clin. Exp. Immunol.* 67: 5–10.

Ramshaw, I. A., ZAndrew, M. E., Phillips, S. M., Boyle, D. B. and Coupar, B. E. H. 1987. *Nature* 329: 545–546.

Reddy, D. N., Reddy, P. G., Minocha, H. C., Fenwick, B. W., Baker, P. E., Davis, W. C., Blecha, F. 1990. Lymphokine Research. 9: 295–307.

Romagnani, S. 1992. Immunol. Today. 13: 379–381.

Seow et al 1994. *Vet. Immunol. Immunopath.* 41: 229–239.

Smith, D. B. and Johnson, K. S., 1988. *Gene,* 67: 31–40.

Snapper, C. M. and Mond, J. J. 1993. *Immunology Today.* 14(1): 15–17.

Staruch, M. J. and Wood, D. D. 1983. *J. Immunol.* 130: 2191–2194.

Valle, A., Aubry, J. P., Durand, I. and Banchereau, J. 1991. *Int. Immunol.* 3: 229–236.

Yilma, T., Breeze, R. G., Risatow, S., Gorham, J., and Leib, S. R. 1985. *Adv. Exp. Med. Biol.* 185: 101.

Zimmerman, G. A., Prescott, S. M. and McIntyre, T. M. 1992. *Immunol. Today.* 13: 93–100.

We claim:

1. An adjuvant composition comprising two cytokines which act in synergy to enhance an antibody response to an antigen wherein the two cytokines are IL-1β and TNF-α or IL-1β and GM-CSF.

2. The adjuvant composition according to claim 1 wherein the two cytokines in said composition are fused together or one or both of each cytokine is fused with another molecule.

3. The adjuvant composition according to claim 1 wherein the adjuvant enhances the antibody response of a human or livestock animal.

4. The adjuvant composition according to claim 1 further comprising an antigen derived from a nematode which antigen comprises Haemonchus contortus tropomyosin.

5. The adjuvant composition according to claim 1 further comprising an antigen derived from a cestode which antigen comprises 45W from Taenia ovis.

6. The adjuvant composition according to claim 2 wherein one or both of the cytokines are fused to glutaione-S-transferase (GST).

7. A multi-compartment pack comprising a first compartment containing a first cytokine comprising IL-1β and a second compartment containing a second cytokine comprising TNF-α or GM-CSF, wherein the first and second cytokines when mixed act in synergy to enhance an antibody response to an antigen and wherein the first and second cytokines are combined with a particular antigen prior to use.

8. A method of enhancing an antibody response in a mammal or a bird to an antigen, said method comprising administering to said mammal or bird an antibody-enhancing effective amount of an adjuvant composition which comprises two cytokines which act in synergy to enhance an antibody response to said antigen in said mammal or bird and wherein the two cytokines are IL-1β and TNF-α or IL-1β and GM-CSF.

9. The method according to claim 8, wherein the mammal is selected from a human, livestock animal, laboratory test animal, a domestic animal and a captive wild animal.

10. The method according to claim 8 wherein the bird is a chicken or other poultry bird.

11. The method according to claim 8 wherein the cytokines are administered sequentially.

12. The method according to claim 8 wherein the cytokines are administered simultaneously.

13. The method according to claim 8 comprising administration of the cytokines with an antigen derived from a nematode which antigen comprises *H. contortus* tropomyosin.

14. The method according to claim 8 comprising administration of the cytokines with an antigen derived from a cestode wherein the cestode antigen is 45W from *Taenia ovis*.

* * * * *

UNITED STATES PATENT AND TRADEMARK OFFICE
CERTIFICATE OF CORRECTION

PATENT NO. : 5,980,911
DATED : November 9, 1999
INVENTOR(S) : Leigh A. Corner et al.

It is certified that error appears in the above-identified patent and that said Letters Patent is hereby corrected as shown below:

Title page,
Line 16, OTHER PUBLICATIONS, "Repsonse" should read -- response --

Column 1,
Line 30, "of integers" should read -- or integers --

Column 3,
Line 8, "acing" should read -- acting --
Line 10, "nay" should read -- may --
Line 42, "TNF-A" should read -- TNF-α --
Line 42, "fictional" should read -- functional --
Line 54, both instances of "EL-1β" should read -- IL-1β --

Column 4,
Line 30, "bukly" should read -- bulky --

Column 5,
Line 19, "chloromercur" should read -- chloromercuri --
Line 27, "imidasole" should read -- imidazole --

Column 7,
Line 16, "an or" should read -- an animal or --
Line 16, "antigens" should read -- antigen --
Line 27, "is" should read -- this --

Column 13,
Line 43, before "concentrations" insert -- Protein --

Column 14,
Line 25, "BamHIand" should read -- BamHI and --
Line 26, "glutaione" should read -- glutathione --
Line 38, "trombin" should read -- thrombin --
Line 58, "4." should read -- 7. --
Line 59, "nature" should read -- mature --
Line 62, "CGCGATCC" should read -- CCGGATCC --

Column 15,
Line 12, "cytotoxcity" should read -- cytotoxicity --

Column 17,
Line 36, "AIOH" should read -- A1OH --

UNITED STATES PATENT AND TRADEMARK OFFICE
CERTIFICATE OF CORRECTION

PATENT NO.    : 5,980,911
DATED         : November 9, 1999
INVENTOR(S)   : Leigh A. Corner et al.

It is certified that error appears in the above-identified patent and that said Letters Patent is hereby corrected as shown below:

Column 18,
Line 53, "M(OH)$_3$" should read -- Al(OH)$_3$ --

Column 20,
Line 19, "Playdair" should read -- Playfair --
Line 43, "Poc" should read -- Proc --

Column 26, claim 6,
Line 49, "glutaione" should read -- glutathione --

Signed and Sealed this

Fifth Day of March, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:1:

GGATCCGCAG CCGTGCAGTC A                                              21

(2) INFORMATION FOR SEQ ID NO:2:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:2:

CCGGTCGACT AGGGAGAGAG GGTTTCCATT C                                   31

(2) INFORMATION FOR SEQ ID NO:3:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:3:

CGCGGATCCC TCAGGTCATC TTCTCAAGCC                                     30

(2) INFORMATION FOR SEQ ID NO:4:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:4:

TCACAGGGCA ATGATCCCAA AGTA                                           24

(2) INFORMATION FOR SEQ ID NO:5:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: CDS (B) LOCATION: 1..27

(xi) SEQUENCE DESCRIPTION: SEQ ID NO:5:

CTG GTT CCG CGT GGA TCC GCA GCC GTC                          27
Leu Val Pro Arg Gly Ser Ala Ala Val
  1               5

(2) INFORMATION FOR SEQ ID NO:6:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO:6:

Leu Val Pro Arg Gly Ser Ala Ala Val
  1               5

(2) INFORMATION FOR SEQ ID NO:7:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..9

(xi) SEQUENCE DESCRIPTION: SEQ ID NO:7:

CTC TCT CCC TAGTCGGGAA TTCAT                                 24
Leu Ser Pro
 10

(2) INFORMATION FOR SEQ ID NO:8:

(i) SEQUENCE CHARACTERISTICS:
            (A) LENGTH: 3 amino acids
            (B) TYPE: amino acid
            (D) TOPOLOGY: linear (ii) MOLECULE TYPE: protein (xi) SEQUENCE DESCRIPTION: SEQ ID NO:8:

Leu Ser Pro
  1

(2) INFORMATION FOR SEQ ID NO:9:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: CDS
            (B) LOCATION: 1..37

(xi) SEQUENCE DESCRIPTION: SEQ ID NO:9:

CTG GTT CCG CGT GGA TCC GCA GCC GTC CTC TCT CCC T AGTCGGGAAT    47
Leu Val Pro Arg Gly Ser Ala Ala Val Leu Ser Pro
      5                  10                  15

-continued

```
TCAT                                                    51

(2) INFORMATION FOR SEQ ID NO:10:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:10:

Leu Val Pro Arg Gly Ser Ala Ala Val Leu Ser Pro
1               5                   10

(2) INFORMATION FOR SEQ ID NO:11:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..37

(xi) SEQUENCE DESCRIPTION: SEQ ID NO:11:

CTG GTT CCG CGT GGA TCC CTC AGG TCA ATT GCC CTG T GAGGGAATTC            47
Leu Val Pro Arg Gly Ser Leu Arg Ser Ile Ala Leu
        15                  20

AT                                                      49

(2) INFORMATION FOR SEQ ID NO:12:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:12:

Leu Val Pro Arg Gly Ser Leu Arg Ser Ile Ala Leu
1               5                   10
```